(12) United States Patent
Koopman et al.

(10) Patent No.: US 7,057,165 B2
(45) Date of Patent: Jun. 6, 2006

(54) PROBE FOR MASS SPECTROMETRY

(75) Inventors: Jens-Oliver Koopman, Babraham (GB); Jonathan M. Blackburn, Babraham (GB)

(73) Assignee: Sense Proteomic Ltd. (GB)

( * ) Notice: Subject to any disclaimer, the term of this patent is extended or adjusted under 35 U.S.C. 154(b) by 0 days.

(21) Appl. No.: 10/329,052

(22) Filed: Dec. 23, 2002

(65) Prior Publication Data

US 2003/0173513 A1    Sep. 18, 2003

(30) Foreign Application Priority Data

| Dec. 21, 2001 | (GB) | ................................ | 0130747 |
| Jul. 15, 2002 | (GB) | ................................ | 0216387 |
| Oct. 25, 2002 | (GB) | ................................ | 0224872 |

(51) Int. Cl.
*B01D 59/44* (2006.01)

(52) U.S. Cl. .................. 250/281; 250/288; 422/68.1

(58) Field of Classification Search ............... 250/281, 250/288; 422/68.1, 61, 50; 435/6
See application file for complete search history.

(56) References Cited

U.S. PATENT DOCUMENTS

| 6,027,890 | A * | 2/2000 | Ness et al. ...................... 435/6 |
| 6,569,383 | B1 * | 5/2003 | Nelson et al. .............. 422/68.1 |
| 6,612,686 | B1 * | 9/2003 | Mutz et al. ..................... 347/46 |
| 6,783,672 | B1 * | 8/2004 | Tubbs et al. ............. 210/198.2 |
| 2002/0177696 | A1 * | 11/2002 | Sun et al. ................. 536/23.1 |
| 2003/0017464 | A1 * | 1/2003 | Pohl .............................. 435/6 |
| 2003/0045694 | A1 * | 3/2003 | Chait et al. ................ 536/23.1 |

OTHER PUBLICATIONS

Brockman, A.H., et al., Probe-Immobilized Affinity Chromatography/Mass Spectrometry Anal.Chem. 1995, 67 (24) pp. 4581-4585.

Gaven, Anne-Claude, et al., Functional organization of the yeast proteome by systematic analysis of protein complexes, Nature 2002, 415 (6868) pp. 141-147.

Gygi, Steven P., et al., Quantitative analysis of complex protein mixtures using isotopecoded affinity tags, Nat. Biotech., 1999, 17, pp. 994-999.

(Continued)

*Primary Examiner*—Nikita Wells
*Assistant Examiner*—Anthony Quash
(74) *Attorney, Agent, or Firm*—Ivor R. Elrifi; Mintz Levin Cohn Ferris Glovsky and Popeo PC

(57) ABSTRACT

The present invention relates to a probe for the analysis of one or more analytes, particularly proteins or compounds capable of binding or otherwise interacting therewith, by laser desorption/ionization mass spectrometry, more particularly MALDI MS. It also relates to a protein microarray, a method of producing a protein microarray and a method of analyzing a protein microarray. The probe comprises a support having an electroconductive target surface thereon characterized in that the target surface comprises a micro array having a plurality of discrete target areas presenting one or more analyte capture moieties. Each discrete target area has an area of less than 1000 μm$^2$, more preferably still less than 500 μm$^2$, and more preferably still less than 100 μm$^2$.

81 Claims, 19 Drawing Sheets

Coupling procedures for proteins on surfaces

Random coupling

BCCP-fusion-biotin

Ordered coupling

Neutravidin

PEG-PLL-biotin

Amine coupling

PEG-PLL

OTHER PUBLICATIONS

Hutchens, T.W., et al., New Desorption Strategies for the Mass Spectrometric Analysis of Macromolecules, Rapid Communications in Mass Spectrometry, 1993, 7, pp. 576-580.

Karas, M., et al., Laser Desorption Ionization of Proteins with Molecular Masses Exceeding 10,000 Daltons, Anal. Chem., 1988, 60 (20) pp. 2299-2301.

Kukar, T., et al., Protein Microarrays to Detect Protein-Protein Interations Using Red and Green Fluorescent Proteins, Analytical Biochemistry 2002, 306, pp. 50-54.

MacBeath, Gavin, Printing Proteins as Microarrays for High-Throughput Function Determination, Science 2000, 289, pp. 1760-1763.

MacBeath, Gavin, Proteomics comes to the surface, Nature Biotechnology, 2001, 19, pp. 828-829.

Ruiz-Taylor, et al., Monolayes of derivatized poly(L-lysine)-grafted poly(ethylene glycol) on metal oxides as a class of biomolecular interfaces, Proc. Nat'l Acad Sci USA, 2001, 98 (3) pp. 852-857.

Schweitzer, B. et al., Multiplexed protein profiling on microarrays by rolling-circle amplification, Nature Biotechnology 2002, 20, pp. 359-365.

Wang, S., et al., Identification of Prostate Specific Membrane Antigen (PSMA) As the Target of Monoclonal Antibody 107-1A4 By Proteinchip; Array, Surface-Enhanced Laser Desorption/Ionization (SELDI) Technology, Int. J. Cancer, 2001 92 (6), pp. 871-876.

Zhu, Heng, et al., Global Analysis of Protein activities Using Proteome Chips, Science, 2001, 293 pp. 2101-2105.

Zhu, Heng, et al., 'Omic' approaches for unraveling signaling networks, Current Opinion in Cell Biology 2002, 14, pp. 173-179.

Borrebaeck et al. (2001). *BioTechniques 30*: 1126-1131.

Davies et al. (1999). *BioTechniques 27*: 1258-1261.

Nelson et al. (2000). *Electrophoresis 21*: 1155-1163.

Thulasiraman et al. (2001). *BioTechniques 30*: 428-432.

Weinberger et al. (2000). *Pharmacogenomics 1*: 395-416.

* cited by examiner

Experimental Section

Matrix formulation for protein microarray

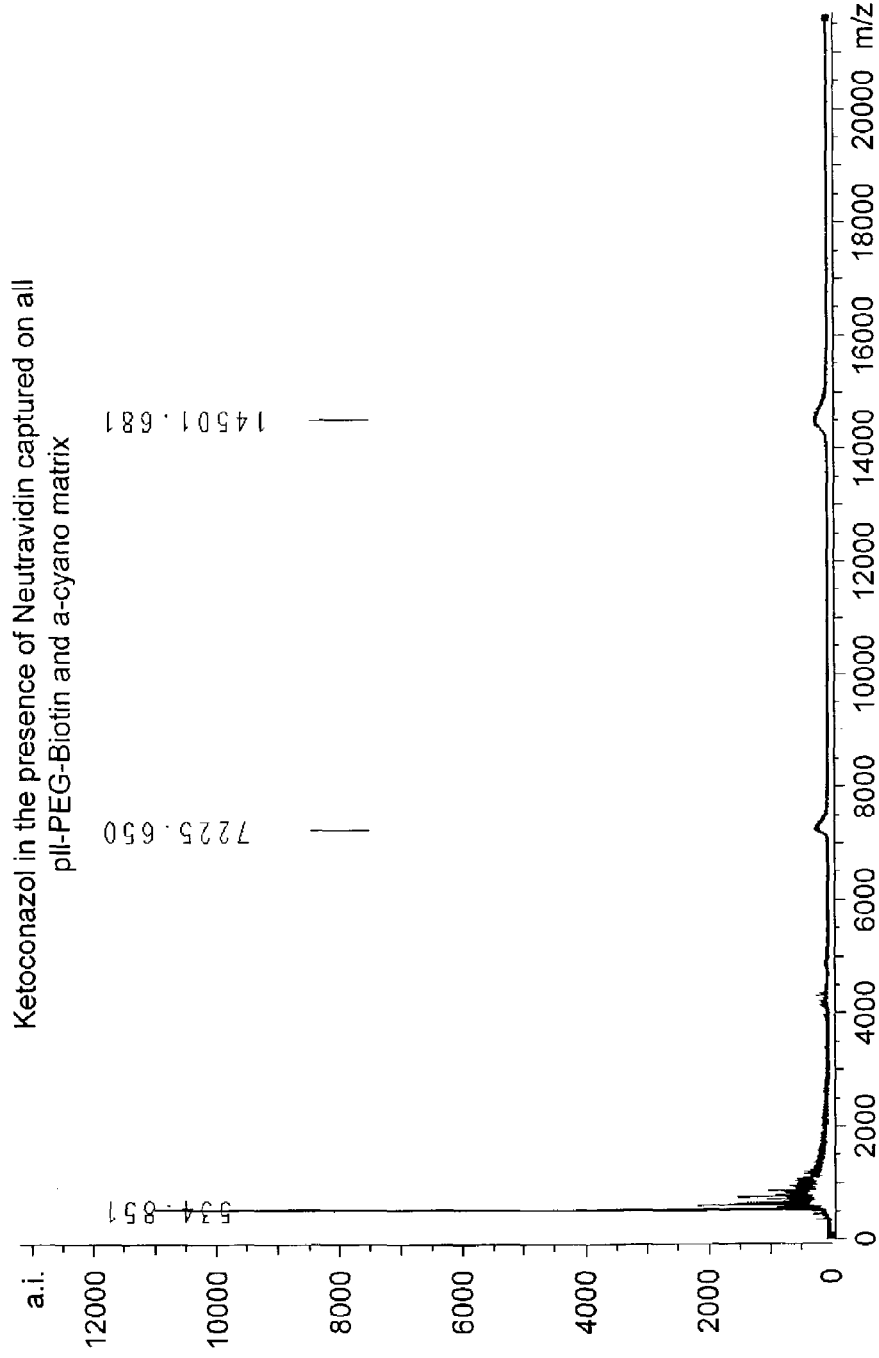

Coupling procedures for proteins on surfaces

Ordered coupling

BCCP-fusion-biotin

Neutravidin

PEG-PLL-biotin

PEG-PLL

Random coupling

Amine coupling

Table 1

| Peptide masses [M+H]$^+$ | Glutathione-S-transferase | Trypsin | Avidin |
|---|---|---|---|
| 770.416 | X | | |
| 919.52 | X | | |
| 963.497 | X | | |
| 1026.563 | X | | |
| 1032.574 | X | | |
| 1094.56 | X | | |
| 1138.518 | X | | |
| 1149.628 | X | | |
| 1182.645 | X | | |
| 1314.736 | X | | |
| 1516.828 | X | | |
| 2326.1 | X | | |
| 845.5 | | X | |
| 2211.1 | | X | |
| 2283.094 | | X | |
| 919.53 | | | X |
| 1235.48 | | | X |
| 1595.845 | | | X |
| 2003.022 | | | X |

PROBE FOR MASS SPECTROMETRY

The present invention relates to a probe for the analysis of one or more analytes, particularly proteins or compounds capable of binding or otherwise interacting therewith, by laser desorption/ionisation mass spectrometry, more particularly MALDI MS; It also relates to a protein microarray, a method of producing a protein microarray and a method of analysing a protein microarray.

Such a mass spectrometry probe, upon which a microarray has been fabricated, enables interrogation of protein—small molecule interactions in a label-free manner by desorption and ionisation of analytes (e.g. protein, drug or drug candidate, carbohydrate, DNA, RNA or other test molecule). The probe and methods are particularly useful in the drug discovery process, for example in hit series evaluation, lead optimisation, predictive toxicogenomics and metabolite profiling.

Analysis of disease processes and drug effects have traditionally focussed on genomics, whereas proteomics, the study of the expressed fraction of a genome, offers a more direct analysis of proteins and their inter-action. Proteomics was initially the quantitative and qualitative study of whole cell, tissue, organ or organism protein expression or fractions thereof. Often it involves comparing samples of similar biological origin exposed to different conditions or comparing diseased and non-diseased tissue. One advantage of proteomics over genomics is that it allows quantitative identification and analysis of proteins; by contrast, genomics can only predict the presence of proteins on the basis of mRNAs that might be translated into proteins. Furthermore, proteomics can identify posttranslational modification of proteins and can therefore draw conclusions about the activity of proteins rather than merely describing its presence.

Conventional analytical methods in proteomics are based on 2D-gel electrophoresis for protein separation followed by proteolytic digestion of the proteins and analysis by mass spectrometry. Alternatively Edman degradation can be used for protein identification after separation. However, both methods suffer limitations due to their bias towards highly expressed proteins and the destructive method of separation. Therefore proteomic methods which avoid the need for 2D-gel electrophoresis, such as isotope coded affinity tag (ICAT, Gygi et al. 1999), tandem affinity protein purification (TAP, Gavin et al. 2002) and protein microarrays (McBeath and Schreiber, 2000), are gaining popularity. Furthermore, these new methods have broadened the scope of proteomics from collecting and cataloguing data to a stage where relations between molecules can be assigned; this is now referred to as functional proteomics.

Protein microarrays have most commonly taken the form of collections of immobilised antibodies that can be used, for example, to monitor protein expression levels in a miniaturised ELISA format (Schweitzer et al. 2002). The use of protein microarrays to analyse the function, rather than simply the abundance, of the immobilised proteins have received limited attention but recent examples include the analysis of substrate specificity within a set of yeast kinases (Zhu et al. 2000) and the identification of calmodulin- and phospholipid-binding proteins within a proteome-scale collection of yeast proteins (Zhu et al. 2001).

To date, protein microarrays have been analysed by enhanced chemo-luminescence (ECL), fluorescent or radioactive labels or via antibody based detection systems, but not by mass spectrometry. The current methods of analysing protein microarrays are therefore restricted by the availability of appropriate labelled ligands. Examples of labelled ligands that have been used successfully include fluorescently-labelled antibodies and radio- or fluorescently-labelled small molecule ligands. However, for drug-like small molecules, which often have molecular weights of less than 1000 Da, neither radio- or fluorescent labels are desirable; radiolabels are disfavoured for health and safety reasons, whilst the introduction of a fluorophore into the small molecule could significantly perturb the structure activity profile in an unpredictable manner. It is therefore clear that a label-free method to detect interactions in a microarray format would be a major advance and would greatly broaden the range of applications to areas where labelled compounds are not available or where labelling would alter the properties of the ligand. This would be particularly useful in the early stage of drug discovery, where great numbers of compounds are screened against proteins.

Amongst the label-free detection methods that are currently available, mass spectrometry has the unique advantage of being able to determine not only the presence but also the identity of a given ligand. However, the development of a MALDI MS-compatible protein microarray is complex since existing methods for forming protein microarrays do not transfer readily onto to a MALDI target. There are a number of reasons why this is the case, inter alia the specialised nature of the probe surfaces and the potential for salts present in reaction buffers to interfere with the detection method. In addition, procedures known in the art for MALDI typically require the co-crystallisation of the aqueous analyte with acidic energy absorbing molecules, or 'matrix', to promote ionisation of the analytes (Karas and Hillenkamp, 1988). The method of co-crystallising analyte and matrix for MALDI, as known in the art, typically results in a heterogeneous crystallisation process and yields discrete, spatially separated crystals that each contain differing amounts of matrix and analyte. As a consequence it is often observed that individual crystals contain insufficient analyte for analysis by MALDI. This in turn results in a requirement for the analyser to sample multiple (ie. 10–100 or more) discrete locations within a given target area in order to obtain a good analyte signal; this is sometime referred to as "the search for the sweet spot" and imposes a significant lower limit on the size of individual target areas that can be routinely interrogated by MALDI MS methods known in the art. Infact, the target area generally has as area of at least 0.5 $mm^2$.

In order to generate MALDI MS-compatible protein microarrays, solutions for the aforementioned shortcomings of the prior art are required that enable both miniaturisation of the target areas and functional analysis of the arrayed proteins.

Some examples of the affinity capture of analytes for mass spectrometric analysis have been described to date. However these examples relate to the use of single antibodies, nitriloacetic acid, anion exchangers or cation exchangers immobilised on the surface of the MALDI target or the use of bead based affinity capture reagents (Hutchens and Yip, 1993, Brockman and Orlando 1995, Wang et al 2001). However, all these methods suffer from one or more of the following limitations:

a) Partial or total loss of biological activity because of amine-based coupling of the analyte or the bait onto the probe;

b) Low specificity between the analyte and the surface which can lead to the non-specific binding of several analytes to the surface (e.g. ion-exchange surfaces);

c) Low affinity of the analyte to the surface which can lead to leaching of the analyte from the surface during any wash procedures (e.g. ion-exchange and nitriloacetic acid surfaces);

d) The affinity capture surface lacks non specific protein resistance, which can lead to high levels of non-specific protein binding which would interfere with the analysis of a protein microarray;

e) The availability of only a limited number of affinity capture proteins.

Thus existing methods do not enable the immobilisation of large numbers of different, purified proteins in the form of a MALDI MS-compatible microarray suitable for functional analysis of the muicroarrayed proteins.

SUMMARY OF THE INVENTION

The primary object of this invention is the development of a probe for the production of a protein microarray (as opposed to an array) which can be interrogated by means of laser desorption/ionisation mass spectrometry, particularly matrix assisted laser desorption/ionisation (MALDI).

The invention also relates to methods leading to the production of such a probe, a protein microarray which can be interrogated by means of laser desorption/ionisation mass spectrometry, particularly matrix assisted laser desorption/ionisation (MALDI) and methods of analysing such a probe or protein microarray.

Some of the significant advances leading to the development of such a probe are described in Applicant's co pending application WO 01/57198 and are thus not dealt with in depth herein.

In order to generate MALDI MS-compatible protein microarrays, solutions for the aforementioned shortcomings of the prior art are required that enable both miniaturisation of the target areas and functional analysis of the arrayed proteins.

As defined herein a probe is a support which is capable of acting as a target in analysis by laser desorption/ionisation mass spectrometry, for example matrix assisted laser desorption/ionisation (MALDI). The probe carries the analytes, for example proteins, during such processes and interacts with the repeller lens of the ion-optic assembly found in laser desorption/ionisation time-of-flight (TOF) mass spectrometers of the art, such that the analytes are converted to gaseous ions to permit analysis. For example, the probes of the invention may be derived from targets for MALDI analysis as known in the art, which are treated such that a high-affinity protein binding moiety e.g. streptavidin, avidin or neutravidin molecules are present on the probe surface which bind biotinylated proteins for subsequent analysis. For example, conventional glass or gold MALDI targets may be used.

As defined herein a micro array is an array where the size of the discrete target areas i.e. the individual areas probed by a laser, is in the order of micrometers or less. Whilst at the upper end of the scale, around 1000 micrometers diameter, they may be visible to the naked eye, at the lower end of the scale the discrete target areas will not be clearly distinguished by the naked eye.

The arrays will typically be arranged in matrices comprising several rows and columns. The number of discrete target areas will depend upon what is being screened though it is generally desirable to have a high density of these discrete areas on the probe surface as this will facilitate high through put screening. Typically a probe will comprise at least 10, more preferably at least 100, more preferably at least 1000, and as many as 10,000, or more target areas produced thereon. (Typically a probe surface will have an area of around 10,000 $mm^2$—a Bruker probe has an area of 10292 $mm^2$ although there is no requirement to use the whole of the probe and the microarray can be applied in one or more matrices thereon.) The actual density in a given matrices will depend upon the size of the discrete target area (which will typically be printed as a spot) and the spacing between adjacent spots. Thus the discrete target areas will typically be present at a density of greater than 1 discrete target areas per $mm^2$ within any matrices.

An analyte capture moiety is the moiety which captures the component which is being screened. Preferably, though not essentially the capturing element is a protein although it is possible to have an array in which, for example, small molecules are bound to the surface and thus to screen for proteins.

The term proteins, as used herein, is used to include both whole proteins and sub units or domains thereof.

Fusion protein, as used herein, is used to refer to a protein, which has a tag, for example, a biotinylation consensus sequence or phleomycin/zeocin resistance binding protein attached thereto.

Linker molecules are molecules which function as their name suggests. They are molecules comprising functional groups which allow bridges to be formed between different molecules.

According to a first aspect of the invention there is provided a probe, for use with a laser desorption/ionisation mass spectrometer, comprising a support having an electroconductive target surface thereon characterized in that the target surface comprises a micro array having a plurality of discrete target areas presenting one or more analyte capture moieties.

The development of such a probe will enable high through put screens to be conducted and a plurality of protein interactions to be studied.

Another significant development enabling the "miniaturisation" of a protein array formed on a MALDI target derives from the application of the Applicant's COVET technology described in WO 01/57198. Briefly, using this technology they are able to create from cDNA libraries expressed proteins, which carry a "sequence tag" that can be used to capture the proteins with a high affinity and in a specific orientation on the microarray surface. This firstly enables proteins e.g. a protein library to be stably immobilized such that leaching of protein from the surface is avoided and secondly the oriented immobilisation of the fusion protein onto the surface ensure maximum biological activity.

Yet another significant aspect of the invention, when compared to current protein microarrays, is the provision of such a probe with an electro conductive surface. This surface which includes semi conductive surfaces is essential where the probe is to be subjected to MALDI MS analysis. Whilst the support could be made wholly of an electro conductive material (which term is used herein to include semi conducive materials) it is preferred to coat a rigid support, e.g. a glass, with an electro conductive material such as, for example, gold although any suitable metal, for example, silver, platinum, iridium, wolfram, copper, cobalt, nickel, and iron or mixtures thereof, or a semiconductor e.g. silicon, graphite or germanium could be used.

Where the probe or protein microarray is produced on e.g. a standard size microscope glass slide it can be mounted in an adapter, which carries it into a mass spectrometer. Such an adaptor is described in Applicant's co pending UK application number 216387.1.

A further significant development, and one which may be viewed independently of the specific applications described herein, has been in the way the Applicant has overcome the problems caused by non specific protein binding. The Applicant has overcome this particular problem by providing a layer resistant to non specific protein binding onto the probe surface. More particularly, the microarray surface is modified by the inclusion of a layer of molecules which repel proteins. These protein repellant molecules which include, for example, polyethyleneglycol may be bound to the probe surface via a linker, such as, for example, a poly amino acid which readily binds to e.g. a glass or gold surface and whose amino or carboxyl side groups can be used to bind the protein repellant molecules such that they reach out from the probe surface. The skilled man will appreciate that other functionalized molecules could be used. Preferably the analyte binding moieties are incorporated in a position where they extend out from the surface. Preferred protein binding moieties include e.g. biotin, biotin-neutravidin, and bleomycin, and these and other moieties can be incorporated into the layer either via these functional groups on the linker molecules and/or via functional groups on the protein repellant molecules. Typically the affinity capture moieties are incorporated in small proportions (typically less than 20%) relative to the protein repellant molecules.

In this way the Applicant has been able to introduce the protein capture moieties not only in a homogeneous, spatial defined arrangement but also in a manner which enables high affinity binding in a specific manner. The resulting surface combines selectivity for the capture of biological macromolecules on the probe with reduced non specific binding of the type commonly observed on underivatised glass or metal surfaces and additionally results in a homogeneous distribution and orientation of the captured biological macromolecules.

The component molecules responsible for repelling non specific proteins include molecules which are generally hydrophilic in nature. They include polymers, such as, for example, polyethylene glycol, dextran, polyurethane and polyacrylamide and self assembled monolayers (SAM). Preferably the polymers comprise one or more functional side groups via which the protein capturing moieties can be attached. In the case of polyethylene glycol the functional group is a hydroxyl group. The molecules responsible for repelling non specific proteins may be bound directly to the surface as in, for example the case of SAM's or they may be attached via a linker. Particularly preferred as linkers are poly amino acids such as, for example, poly L lysine, poly L aspartic acid, poly L glutamic acid or mixtures thereof. These have amino or carboxy side chains via which the molecules responsible for repelling non specific proteins can be attached and which can additionally be used to attach the protein capturing moieties. Alternatively, or in addition, the protein capturing moieties can be attached via the component molecules responsible for repelling non specific proteins. FIG. 7 illustrates the binding of such molecules and contrasts the defined orientation which can be achieved by this ordered coupling compared to that achieved using current antibody binding techniques which result in random coupling.

In a preferred embodiment the probe has as it's protein capture moieties either a biotin binder e.g. neutravidin, avidin or streptavidin or a bleomycin resistant protein binder e.g. bleomycin. The proteins are bound to the probe to create a protein microarray by printing a plurality of bacterial, yeast, sf9 or mammalian cell lysates containing fusion proteins in which a high affinity tag e.g. biotin or zeocin resistant protein (ZRP) is expressed onto the capture surface. Proteins are derived from the expression of a cDNA library and each individual clone is tagged at the C-terminus and/or on the N-terminus with a consensus sequence, which will enable high affinity recognition of the protein even in the presence of the otherwise protein repellent molecules. Only the recombinant, tagged protein can recognise the capture surface and other proteins from the lysate can be washed away as they do not bind to the protein repellent surface and do not have a high affinity to the protein binding moieties present in the layer.

Another aspect of the invention is the study of the full protein complement, or a significant fraction thereof, of given cell or tissue type using a probe or protein microarray according to the invention.

According to a further aspect of the present invention there is provided a method of producing a protein microarray for use with laser desorption ionisation mass spectrometer comprising providing a probe of the invention and depositing protein in registration with the protein capturing moieties in the discrete target area.

According to a further aspect the invention utilizes the probes and protein microarrays to analyse and screen various reactions.

One method of analysis by laser desorption/ionisation mass spectrometry comprises the steps of:
 a) providing a probe of the invention;
 b) bringing said probe into contact with one or more proteins; and
 c) performing laser desorption/ionisation mass spectrometry on the proteins on the surface of the probe.

In one embodiment the method comprises, between step b) and c), an additional step of removing unbound molecules from the probe by washing.

In another embodiment the one or more proteins are contained in a mixture of proteins.

In yet a further embodiment, which is a method for identifying a protein on the surface of the probe, the method comprises the additional steps of:
 d) determining the mass of the protein molecule;
 e) performing a digestion upon a replicate sample of said protein on a further probe or probe surface; and
 f) performing laser desorption/ionisation mass spectrometry on the peptides resulting from step e) to identify said protein(s).

In another embodiment there is a method for analysing the function of a protein on the surface of the probe and a molecule interacting with said protein and which comprises the alternative and additional steps of:
 c) bringing a protein on the probe surface into contact with one or more (test molecules;
 d) removing unbound test molecules from the probe surface;
 e) performing laser desorption/ionisation mass spectrometry on the protein and any molecule that had been specifically retained on the probe surface through interaction with the protein to determine the identity of the protein and/or test molecule.

The test molecule may be a small molecule, protein, or a nucleic acid e.g. DNA or RNA.

In a further embodiment there is a method for analysing the function of a protein on the surface of the probe and a molecule interacting with said protein and which comprises the alternative and/or additional steps of:
 c) bringing a protein on the probe surface into contact with one or more test substrates; and d) performing laser desorption/ionisation mass spectrometry on the protein and test substrates to determine the presence and/or identity of products of catalysis of said test substrates by the protein.

In one embodiment a cDNA library which has been cloned to express a high affinity tag is expressed and after expression of each clone, the tagged library proteins are captured by the protein affinity moieties and dried onto the microarray, overlaid with a proteolytic agent of biological or chemical origin, cleaved into fragments, overlaid with energy absorbing matrix molecules prepared in a non-aqueous solvent that is spiked with and anti evaporative agents such as glycol. The energy absorbing molecules are applied to the protein microarray in a new formulation at volumes of e.g. a few nanoliters to form a continuous layer of microcrystals.

This use of energy absorbing molecules in this way is yet another and independent aspect of the invention.

According to a further aspect of the present invention there is provided a solution comprising energy absorbing matrix molecules, a non-aqueous solvent and an anti evaporative agent.

According to a further aspect of the present invention there is provided a method of analysing a probe of the invention in which energy absorbing molecules are deposited in a manner which denatures and thus unbinds a protein from a protein capturing moiety leaving the denatured protein lying unbound on the surface.

The energy absorbing molecules form a homogenous layer of crystals in discrete locations in registration with the protein capturing moieties and captured protein.

The homogenous layer of crystals is substantially continuous such that individual crystals are not visible at a 100 fold magnification and there are no visible gaps. It also has a substantially uniform depth, such that there is no apparent variation in crystal size at a 100 fold magnification.

The energy absorbing molecules are deposited onto the surface in a non aqueous solvent and the non aqueous solvent is evaporated off. Preferably the non aqueous solvent is an organic solvent, such as, for example, acetone or butanone. Preferably the non aqueous solvent includes a modifier which controls the rate of evaporation such that crystallisation of the energy absorbing molecules occurs on the probe. Suitable modifiers include glycerol, polyethyleneglycol and thioglycerol. Preferably the energy absorbing molecules are deposited in a mixture of from 80–99.9%, preferably 99% organic solvent e.g. acetone to 20–0.1%, preferably 1% of modifier e.g. glycerol (vol/vol). Typical energy absorbing molecules include crystals of α-cyano-4-hydroxy-cinnamic acid, sinapinic acid, gentisic acid, nifidine, succinic acid, 1,8,9,-anthracenitriol, 3-Indoleacrylic acid, 2-(hydroxyphenylazo) benzoe-acid, 4-nitroanilin and combinations thereof.

Preferably the energy absorbing molecules are deposited in registration with the protein and each protein spot is overlaid with a similar sized spot of the energy absorbing molecules.

A further application of the protein microarray is the parallel analysis of protein-protein, protein-nucleotide and protein small molecule interaction by mass spectrometry.

Yet another aspect of the invention is its usefulness to screen small molecule compound libraries on the probe to detect binding of drug-like small molecules to proteins that are derived from a proteome, where the small molecules do not carry a label such as a radiolabel or a fluorescent label.

In order to achieve a high density of individual samples on the microarray the energy absorbing molecules need to be arranged in microcrystals on the surface. The matrix forms a homogenous layer of flat crystals without significant gaps between them and can be deposited in very small quantities on the microarray.

In contrast to the prior art in which matrix and analyte are co crystalised in an aqueous solvent, the Applicant uses two distinct steps in which first the protein is deposited in an aqueous solvent and then the energy absorbing molecules are deposited such that they crystallise out from the non aqueous solvent on the probe. This has the advantage that the protein is deposited in its biological form. However, using a non aqueous solvent to deliver the energy absorbing molecules allows the formation of a homogenous layer of microcrystals. This has two benefits. First the formation of a homogenous layer means it is not necessary to search for a sweet spot as the homogenous layer guarantees protein in the presence of energy absorbing molecules and secondly it results in more accurate measurement due to the even nature of the layer.

Another aspect of the invention is the automated analysis of small molecules binding to proteins present on the microarray. The molecular weight of small molecule ions, which are stored in a database can be compared with the measured molecular weight of a compound library and therefore the relationship between the small molecule and protein in the array can be assigned.

The various aspects of the invention will now be described, by way of example only, with reference to the following figures and examples in which:

On the left side (top to bottom) are:
i) α-cyano-4-hydroxy-cinnamic acid;
ii) sinapinic acid; and
iii) gentisic acid.

All have been prepared in 99% acetone, 1% glycerol (v/v).

On the right hand side (top to bottom) are the same matrices
iv) α-cyano-4-hydroxy-cinnamic acid;
v) sinapinic acid; and
vi) gentisic acid.

prepared in aqueous solvents as per the prior art.

Figure 1A:
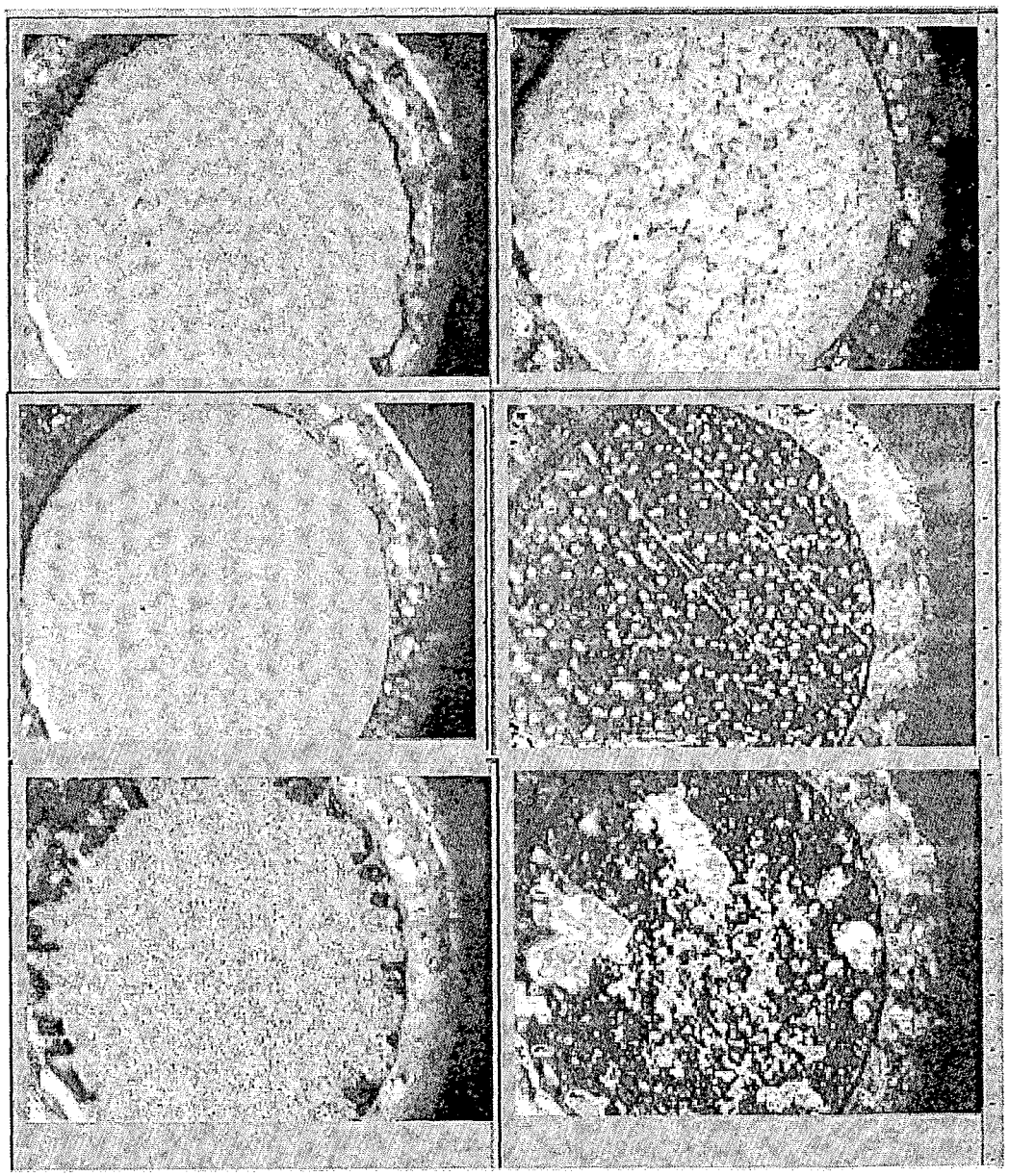
FIG. 1a show six screenshots taken from a Bruker Autoflex mass spectrometer flexcontrol tool comparing the crystal surface of one aspect of the invention with that obtained practicing the method of the prior art. The six screenshots show three different matrices prepared in two different ways.
Figure 1B:
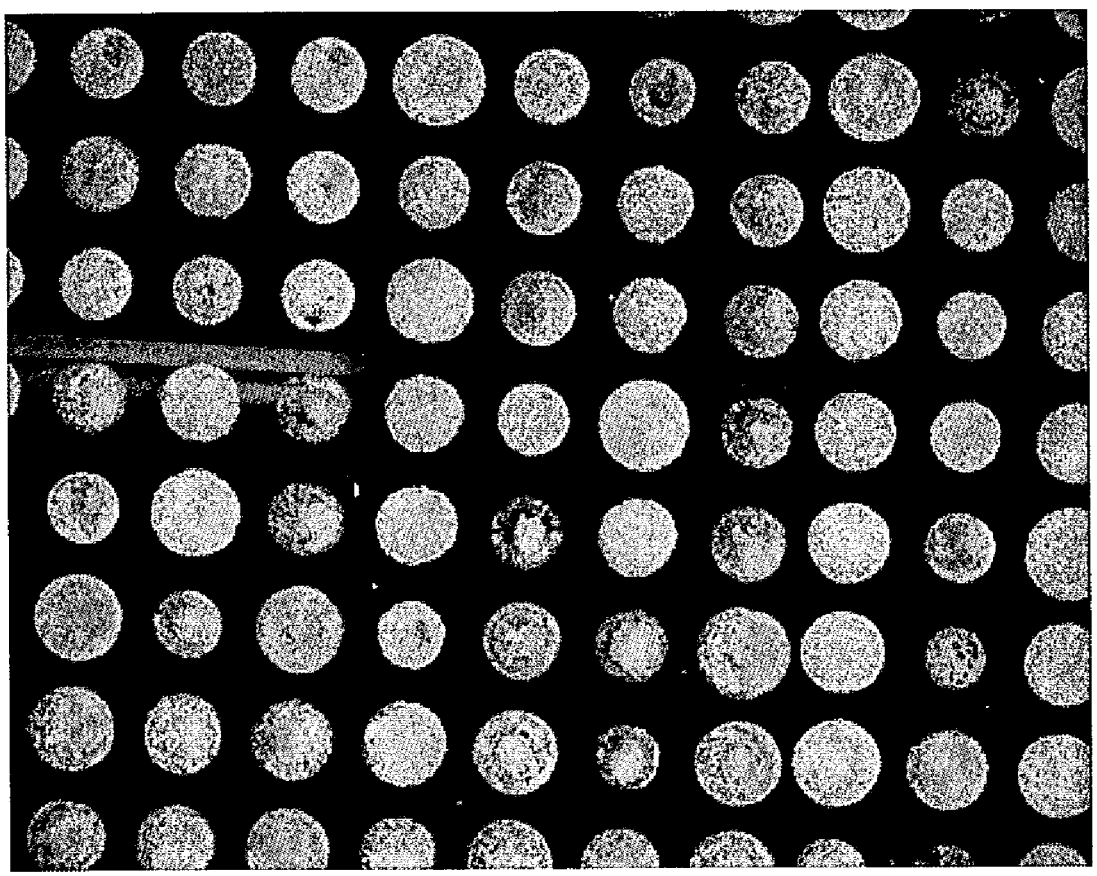

FIG. 1b shows a photomicrograph of α-cyano-4-hydroxy-cinnamic acid crystals. The matrix was dissolved in 99% acetone v/v, 1% glycerol and arrayed onto a gold coated glass slide with an affinity capture surface. The printing density is 562 micrometers from spot center to spot center.

Figure 2A:
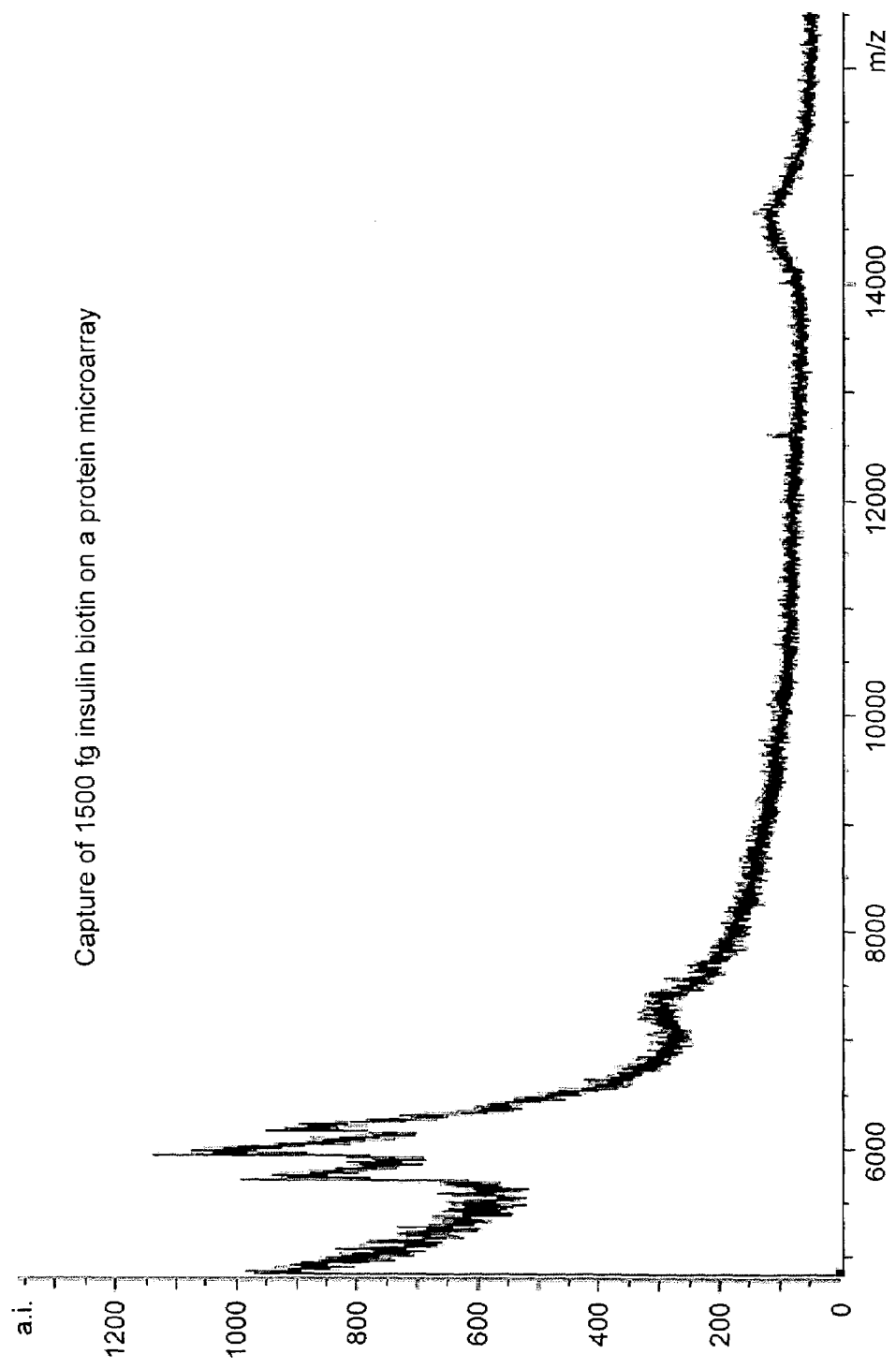

FIG. 2a shows a mass spectrum acquired from a protein microarray demonstrating the capture of 1500 femtogram insulin-biotin on a affinity capture surface. There are three insulin-biotin peaks visible due to different degree of biotinylation. Up to 3 biotin molecules were observed on insulin in the range of 6000 dalton. Two additional peaks are observed at 7300 dalton and 14600 dalton and are assigned as Neutravidin $[MH]^+$ and $[MH]^{2+}$.

Figure 2B:
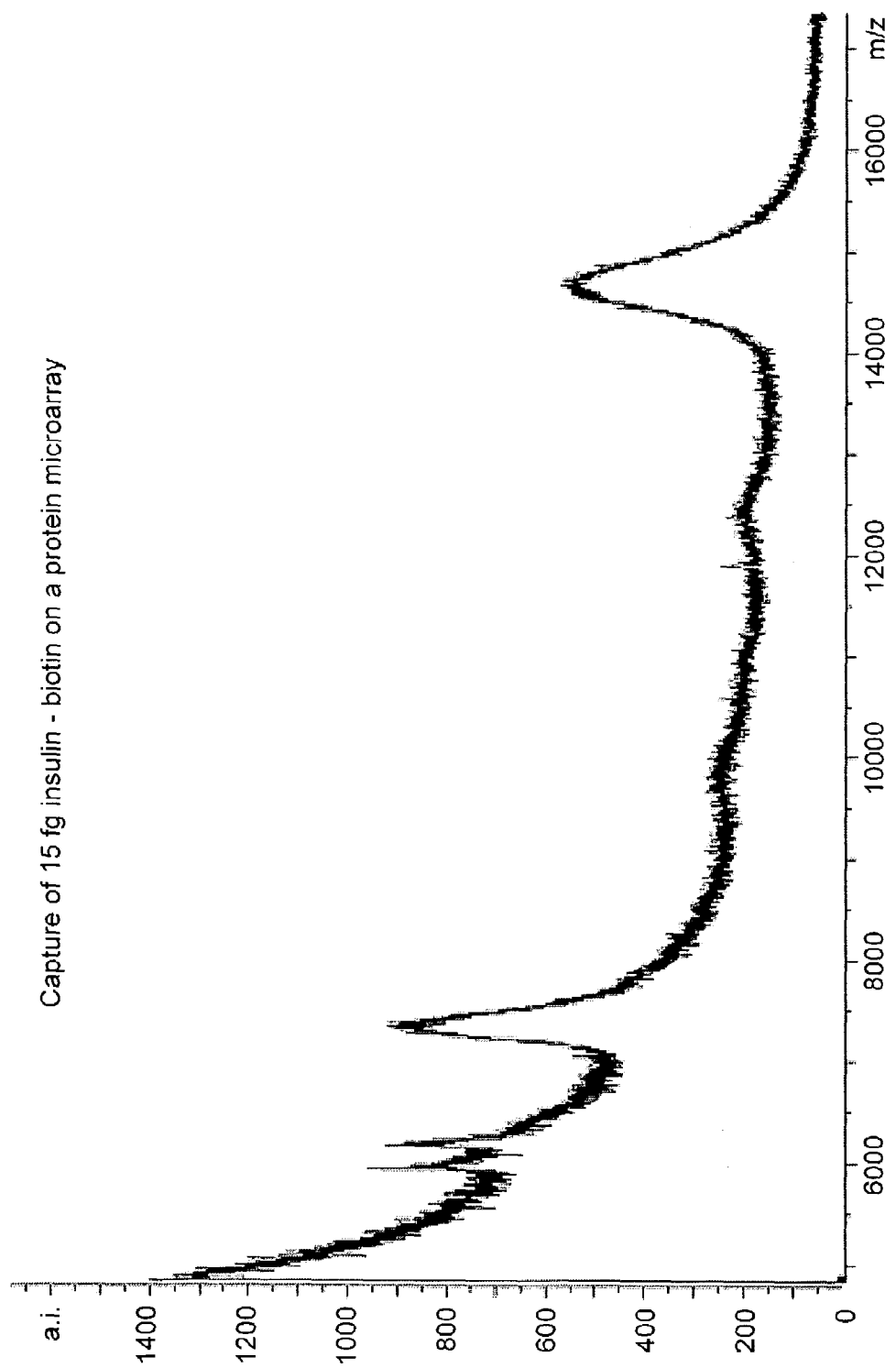

FIG. 2b shows a mass spectrum acquired from a protein microarray demonstrating the capture of 15 femtogram insulin-biotin on a affinity capture surface. Two insulin-biotin peaks are visible in the area of 6000 dalton. Two additional peaks are observed at 7300 dalton and 14600 dalton and assigned as Neutravidin [MH]$^+$ and [MH]$^{2+}$.

Figure 3A:
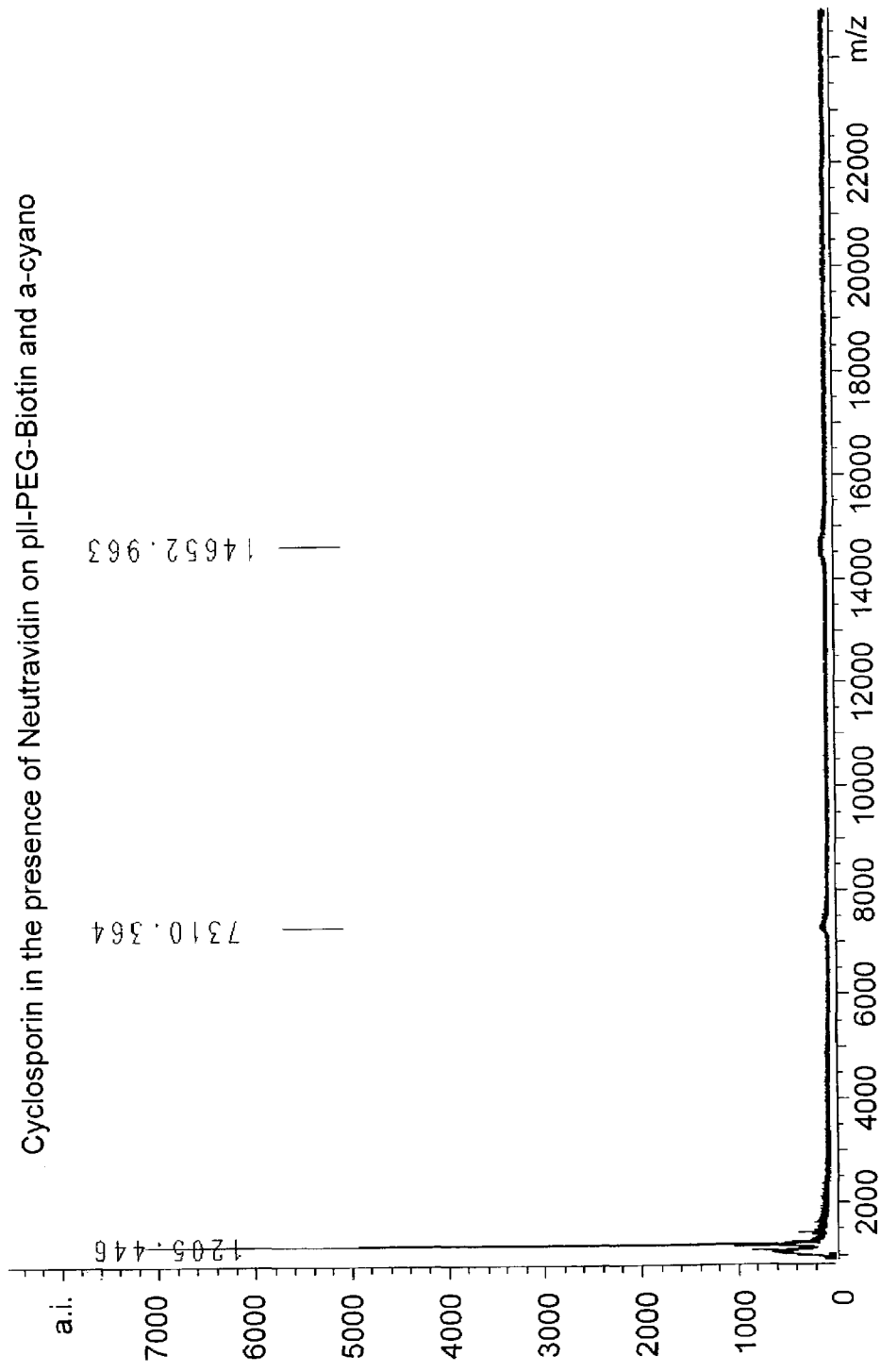

FIG. 3a shows the detection of Cyclosporin by mass spectrometry on a PEG-PLL-Biotin Neutravidin affinity capture surface. Cyclosporin is detected at 1205 dalton and Neutravidin [MH]$^+$ and [MH]$^{2+}$ peaks are present at 7310 and 14652 dalton.

FIG. 3b shows the detection of Ketoconazole by mass spectrometry on a PEG-PLL-Biotin Neutravidin surface. Ketoconazole is detected at 534 dalton and Neutravidin [MH]$^+$ and [MH]$^{2+}$ peaks are at present at 7225 and 14501 dalton.

Figure 3C:
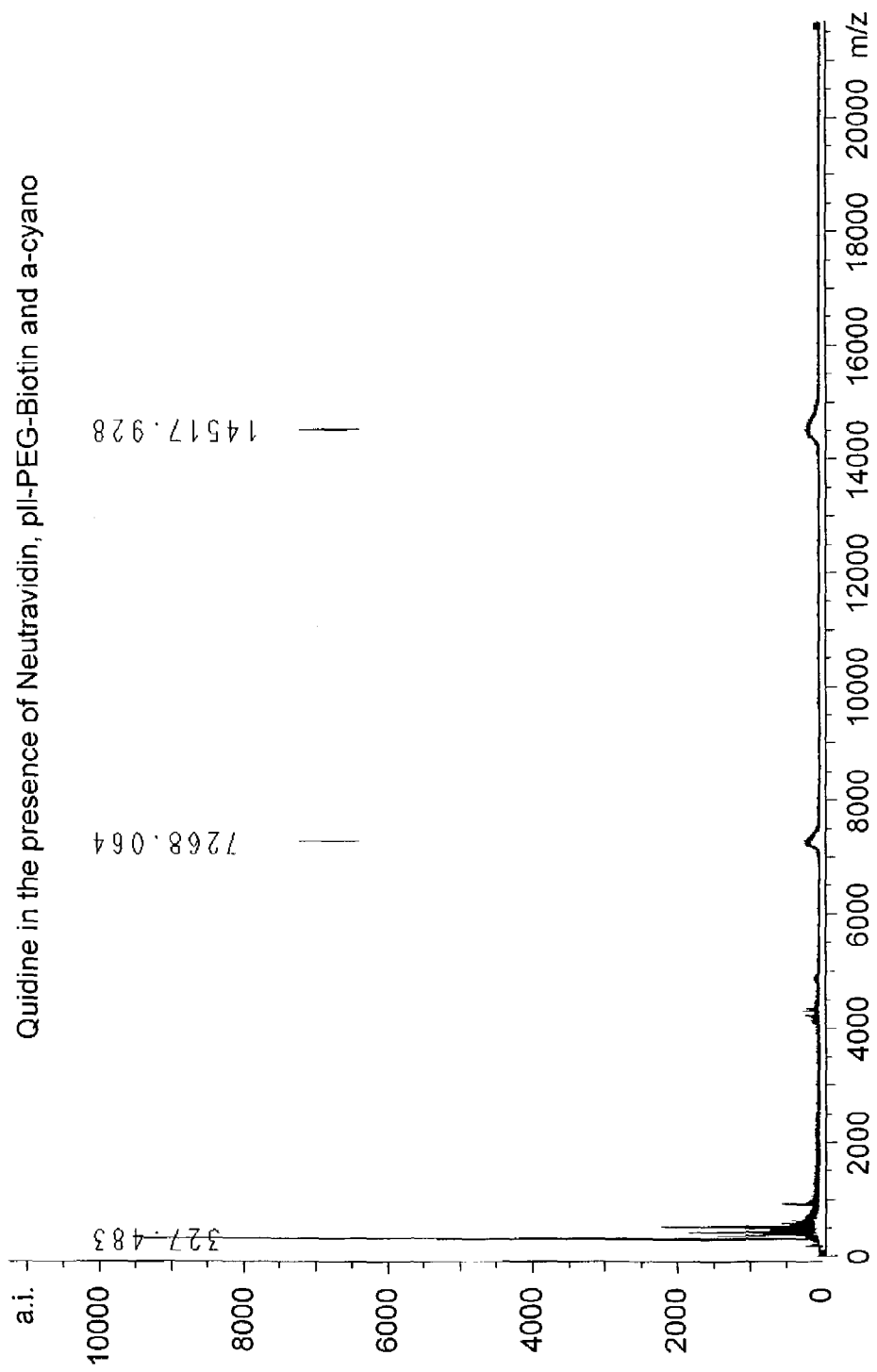

FIG. 3c shows the detection of Quinidine by mass spectrometry on a PEG-PLL-Biotin Neutravidin surface. Quinidine is detected at 327 dalton and Neutravidin [MH]$^+$ and [MH]$^{2+}$ is present at 7310 and 14652 dalton.

Figure 4A:
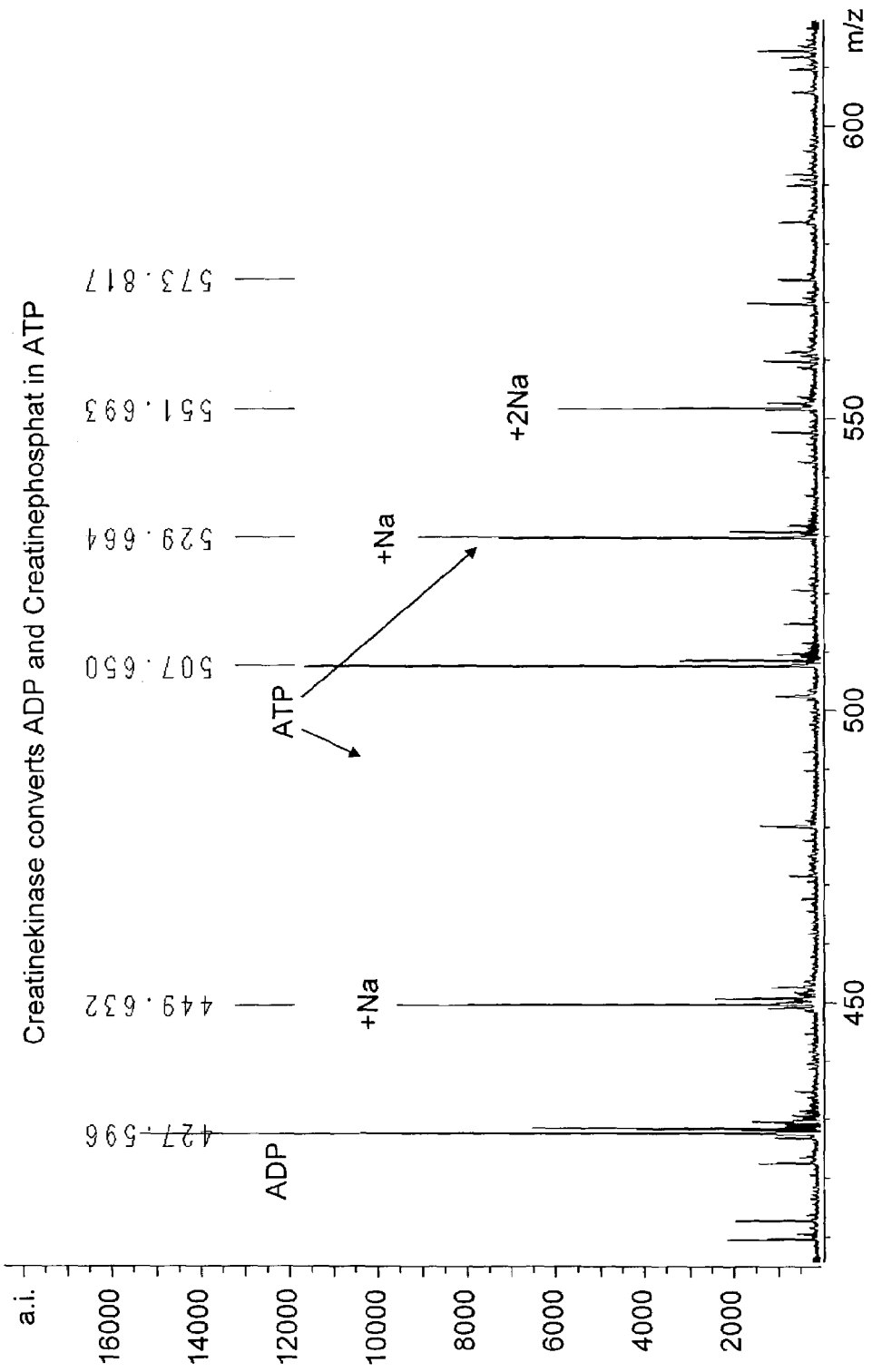

FIG. 4a shows the detection of ADP and ATP. ATP was enzymatically synthesized from the reaction of ADP, creatine phosphate and creatine phosphate kinase in 25 mM ammonium bicarbonate at pH 7.4. [ADP]$^-$ was detected at 427.6 dalton and [ADP+Na]$^-$ 449.6 dalton. The products of the creatine phosphate kinase reaction were detected at 507.6, 529.6, 551.6 and 573.8, which fits well with the expected molecular weight of [ATP]$^-$ and three ATP sodium adducts [ATP Na]$^-$. [ATP Na$_2$]$^-$ and [ATP Na$_3$]$^-$. Control reactions in which either one of the substrates ADP or creatine phosphate or the enzyme creatine phosphate kinase was omitted didn't show ATP peaks.

Figure 4B:
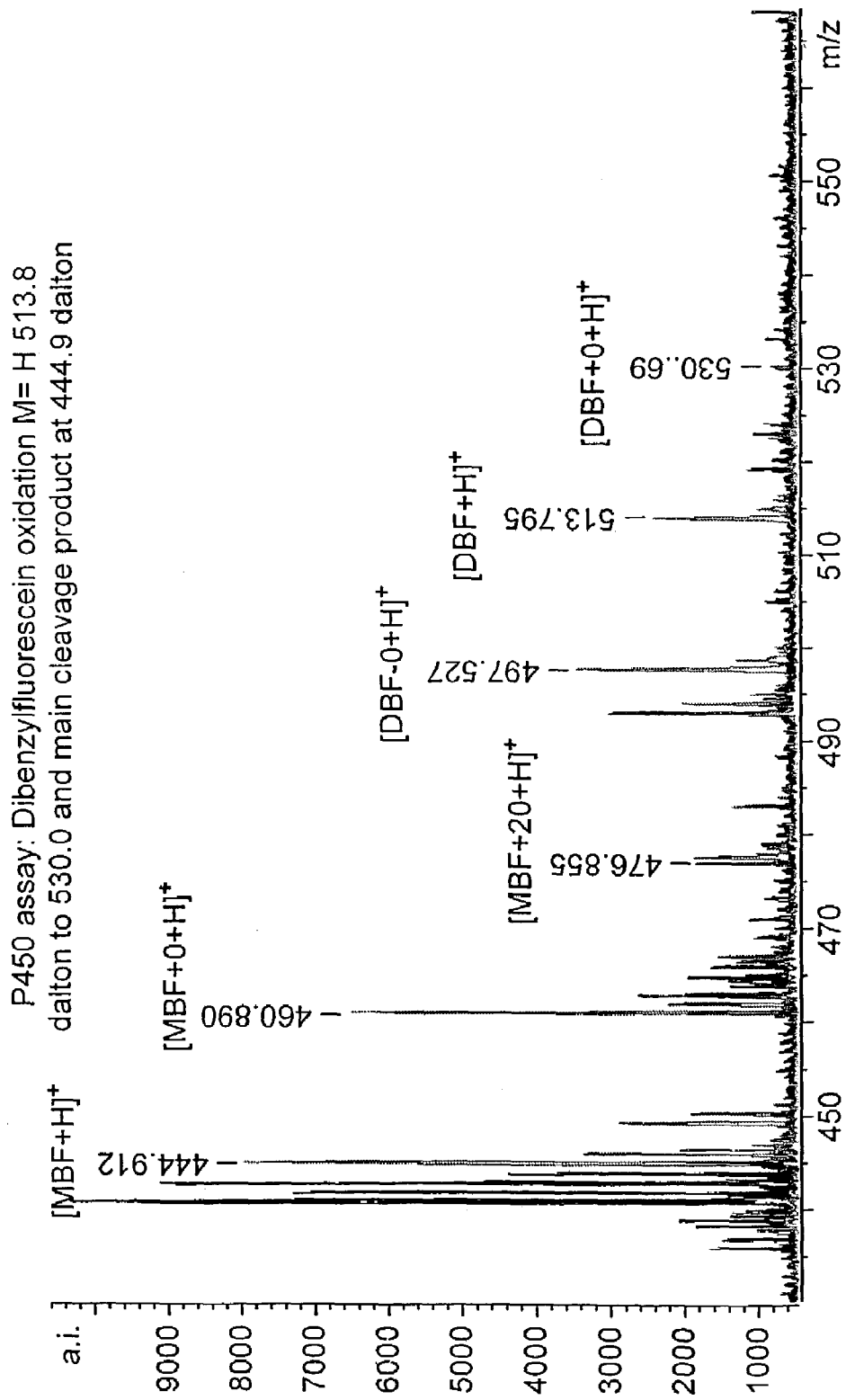

FIG. 4b shows a MALDI mass spectrum detecting human cytochrome p450 oxidation products of dibenzylfluorescine (DBF). DBF was oxidized by cytochrome P450 and a metastabile oxidation product was detected at 530 dalton. Further molecular ions of oxidized dibenzylfluorescine were detect at 477 and 461 dalton presenting two monobenyzlfluorescine derivatives.

Figure 5:
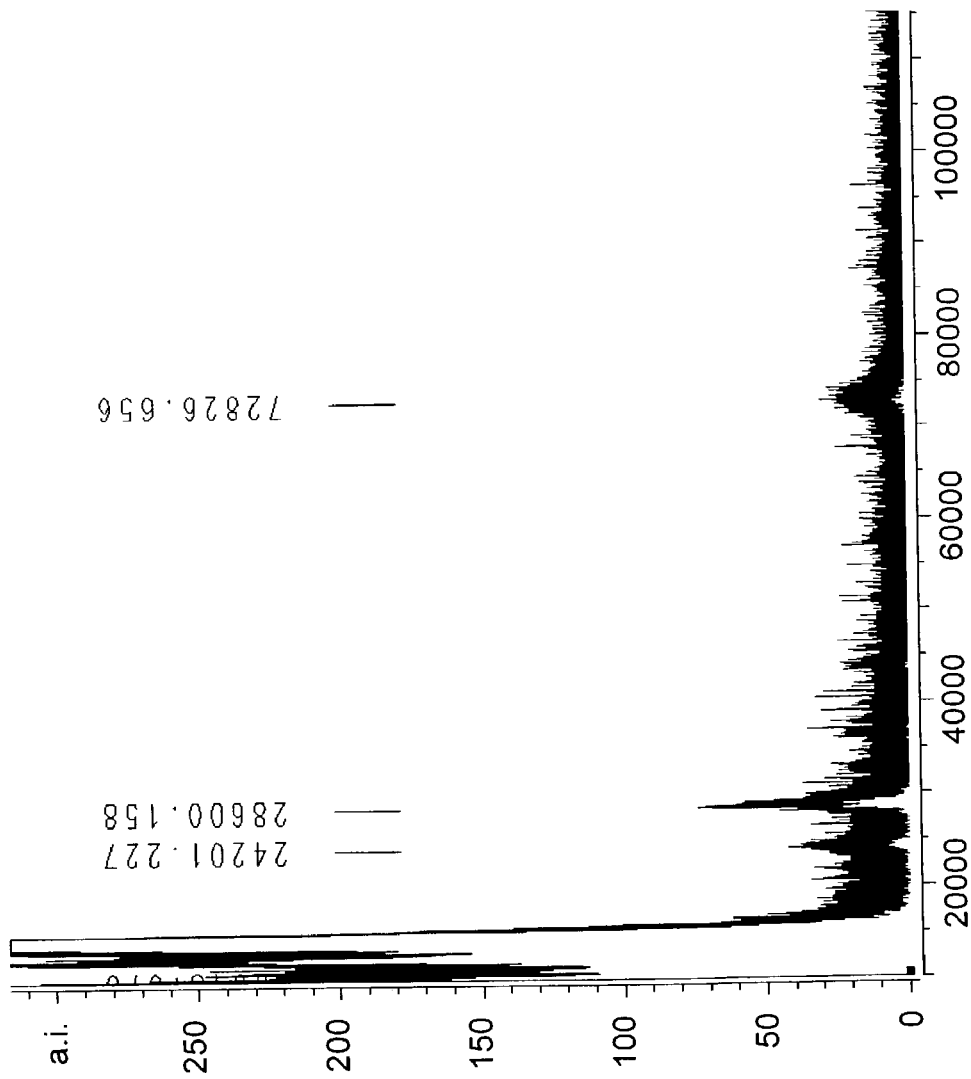

FIG. 5 shows the capture of a biotinylated 72 Kda polypeptide on a PEG-PLL-Biotin Neutravidin coated gold target. The protein was expressed in 200 microliter *Escherichia coli* culture, the bacteria were lysed with lysozyme and Dnase treated. The resulting bacterial lysate was spotted onto a affinity capture surface and incubated for 4 hours. The probe was then washed with 1 mM Tris-HCL pH 7.5 0.1% Triton followed by two washes with 1 mM Tris-HCl pH 7.5 for desalting and removal of detergent. The probe target was then dried under nitrogen and overlaid with energy absorbing matrix (α-cyano-4-hydroxy-cinnamic acid dissolved in acetone). The mass spectrum was acquired in linear mode using the delayed extraction technique at low laser power.

Figure 6:
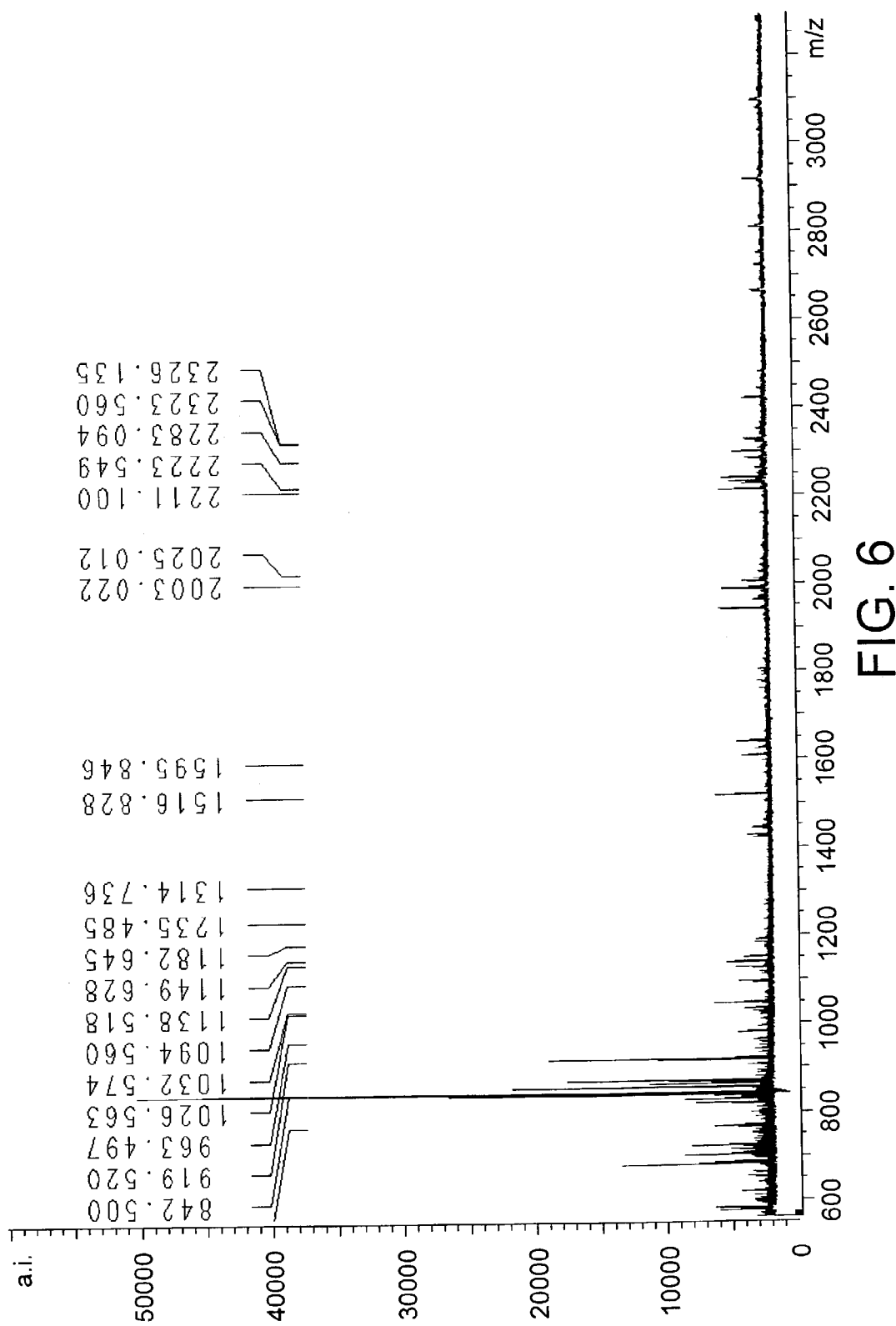

FIG. 6 shows identification of genetically engineered *Schistosoma mansoni* Glutathione-S-Transferase BCCP fusion protein that was expressed in *Escherichia coli*. Glutathione-S-Transferase was captured from a crude bacterial lysate on the probe by the use of affinity capture polymers. The captured analyte was washed and digested on the probe overlaid with energy absorbing matrix dissolved in acetone and analysed by a MALDI TOF mass spectrometer. The resulting peptide masses were used for a protein fingerprint analysis and the fusion protein was identified as Glutathione-S-Transferase from *Schistosoma japonicum*.

Figure 7:
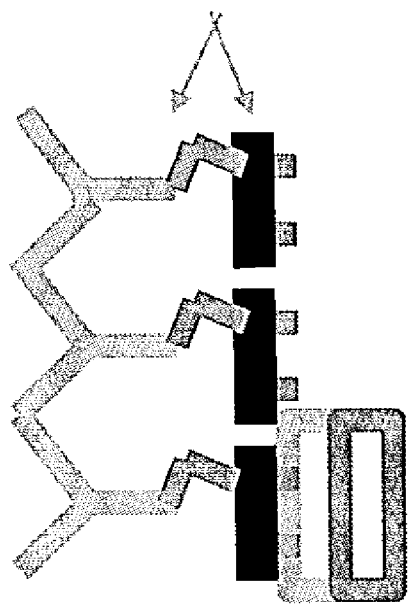
Figure 7:
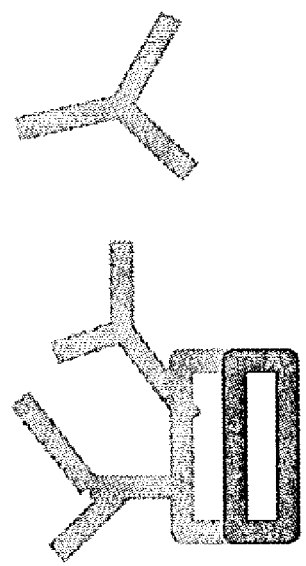

FIG. 7 shows random and orientated coupling of proteins on a probe for example a MALDI target, microtiter plate or a microscope glass slide.

Figure 8:
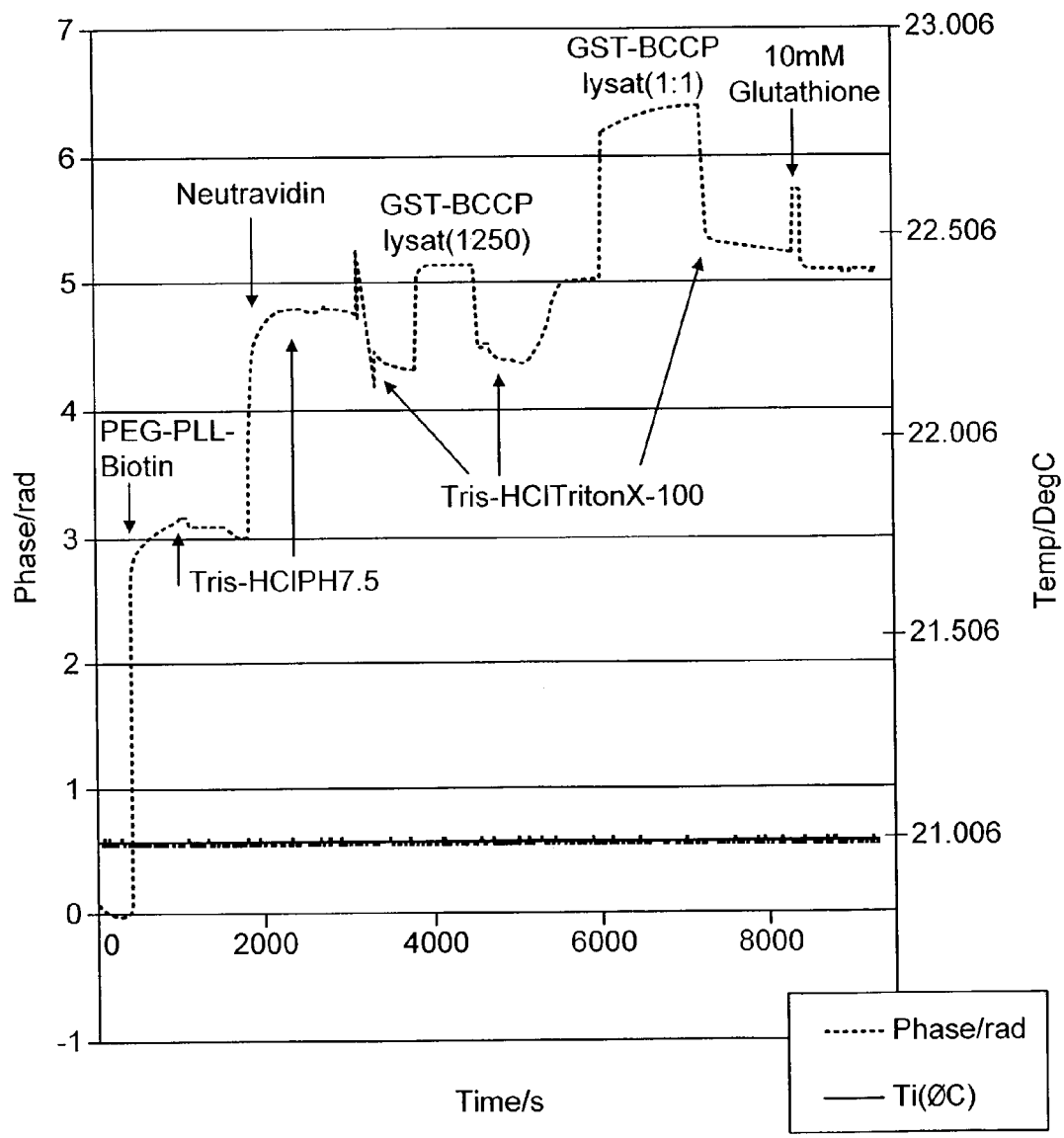

FIG. 8 The binding of poly-L-lysine poly ethylenglycol biotin polymer (PEG-PLL-biotin) to a biosensor is shown. Subsequently, neutravidin and a protein lysate from *E. coli* containing biotin tagged Glutathione-S-transferase (GST-BCCP) was added to the surface followed by a washing period for each step.

Figure 9A:
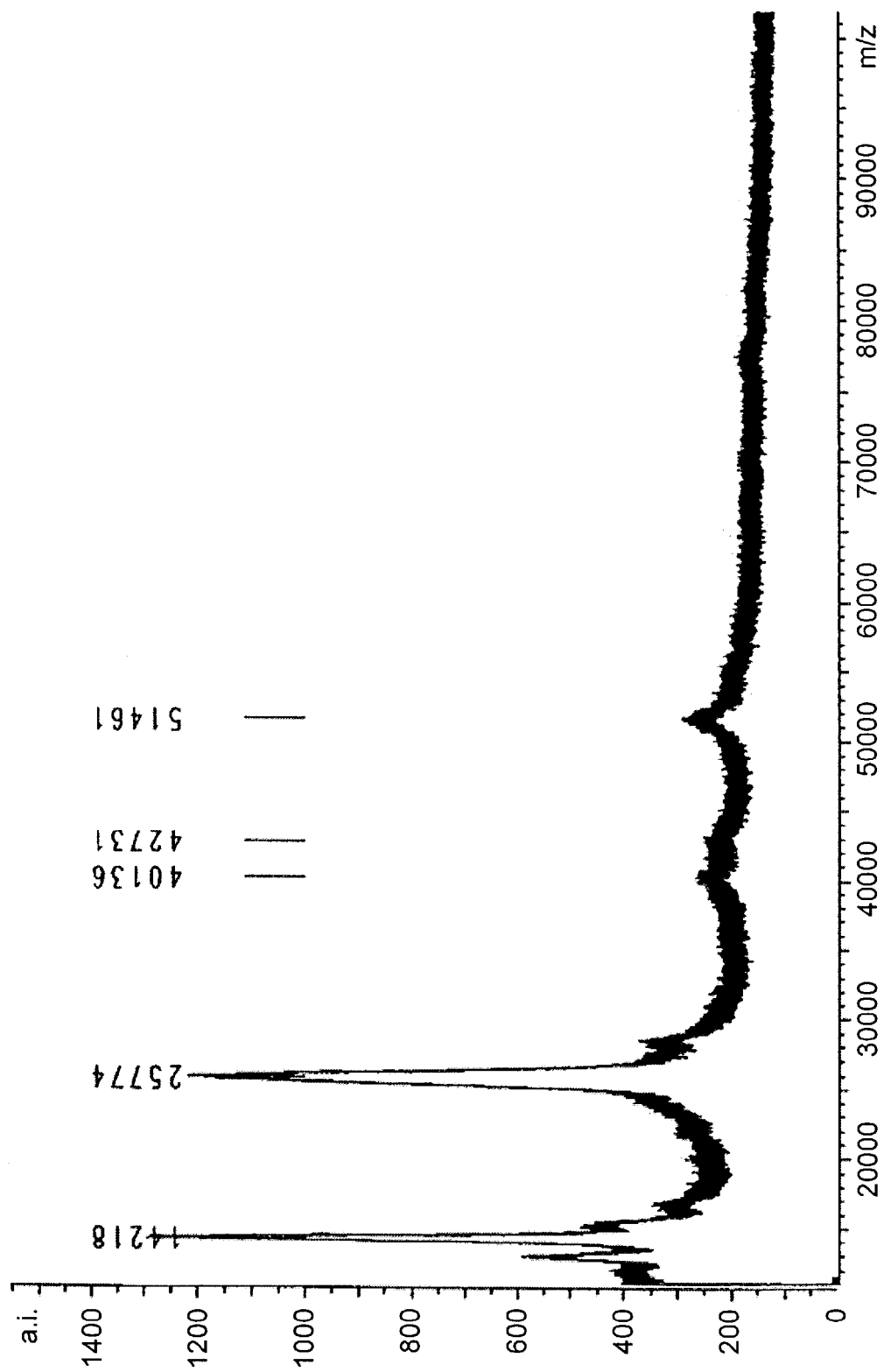
Figure 9B:
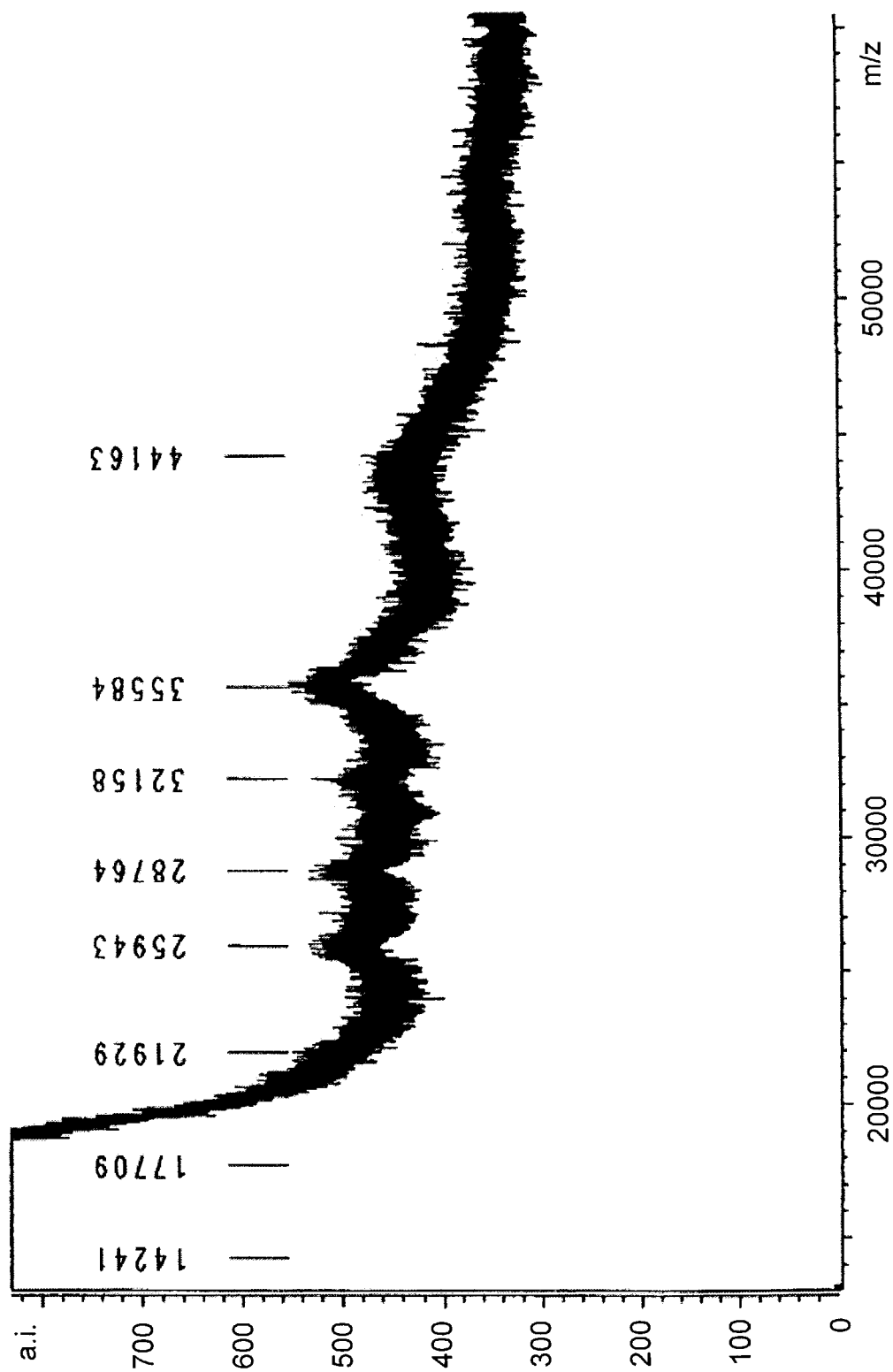

FIGS. 9a and 9b Mass spectra of distinct forms of the glycoprotein Fetuin on immobilised lectins. (a) Biotinylated peanut lectin was immobilised on a PEG-PLL-biotin-neutravidin surface for the capture of the glycoprotein Fetuin. The [M+H]$^+$, [2M+H]$^+$ molecular ions of the lectin were observed at 25774 and 51461 dalton and the [M+H]$^+$ molecular ion of neutravidin was observed at 14300 dalton. Peaks accounting for the molecular ions of the glycoprotein were observed at 40136 and 42731 dalton. (b) Biotinylated wheat germ agglutinin was immobilised on PEG-PLL-biotin-neutravidin surface and used for the specific capture of the glycoprotein Fetuin. The [M+H]$^+$, [2M+H]$^+$ molecular ions of the lectin were observed at 17709 and 35584 daltons and [M+H]$^+$, [2M+H]$^+$ molecular ions of neutravidin were observed at 14300 and 28600 dalton. The [M+H]$^+$ molecular ion of the glycoprotein Fetuin was observed at 44163 dalton and two peaks at 25943 and 32158 daltons were specific for the glycoprotein and represent most likely breakdown products.

Figure 10A:
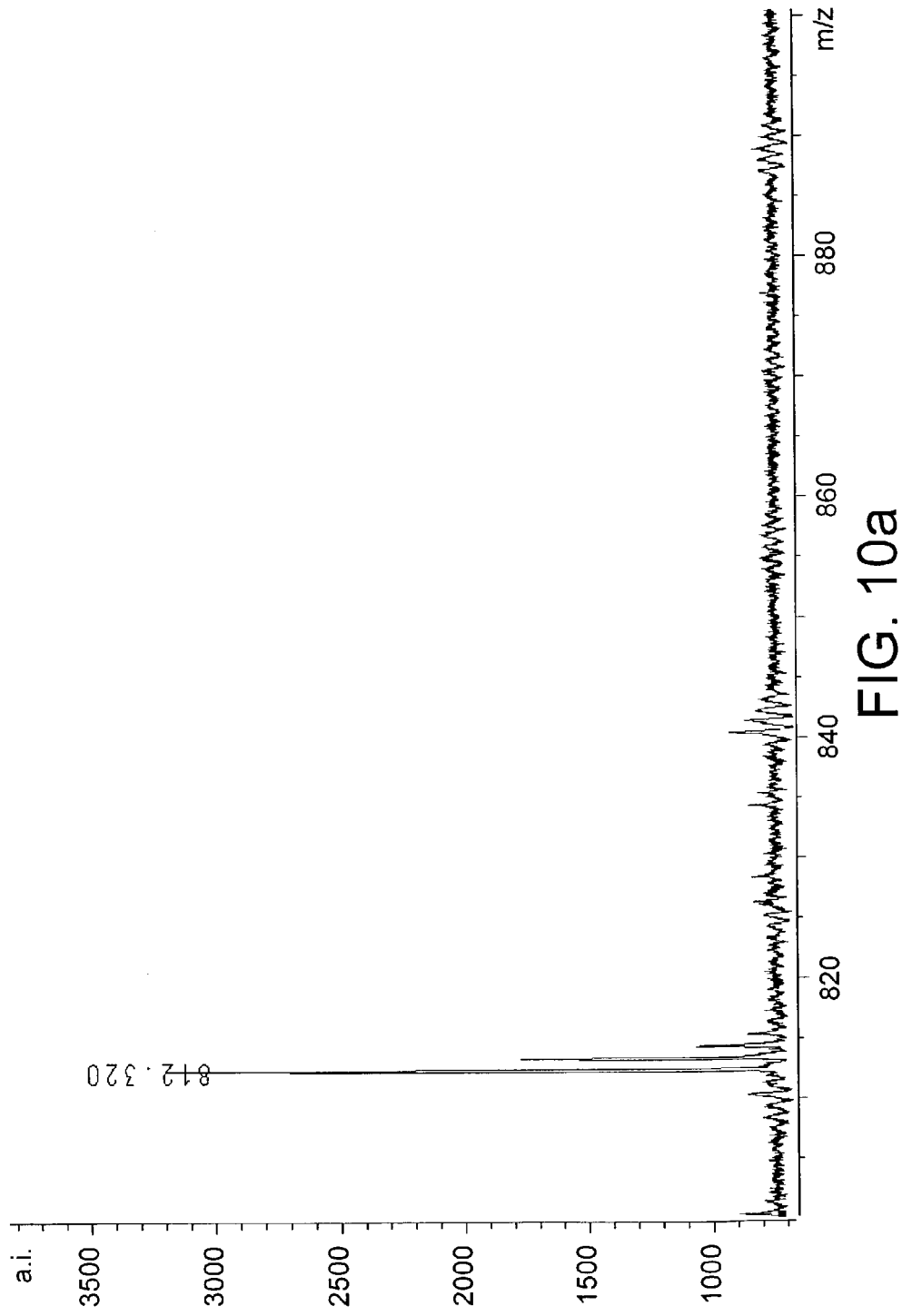

FIG. 10a shows the specific binding of a Rhodamine-lactose derivative to the lectin from *Arachis hypogea*. (a) A PEG-PLL-Neutravidin *Arachis hypogea* surface was overlaid with 1 mM lactose-rhodamine conjugate and washed three times with 1 mM Tris-HCl. pH 7.5 and overlaid with a solution of energy absorbing α-cyanohydroxycinamic acid dissolved in acetone. The following MALDI MS analysis shows a molecular ion at 830.32 dalton which fits with [MH]$^+$ of lactose-rhodamine.

Figure 10B:
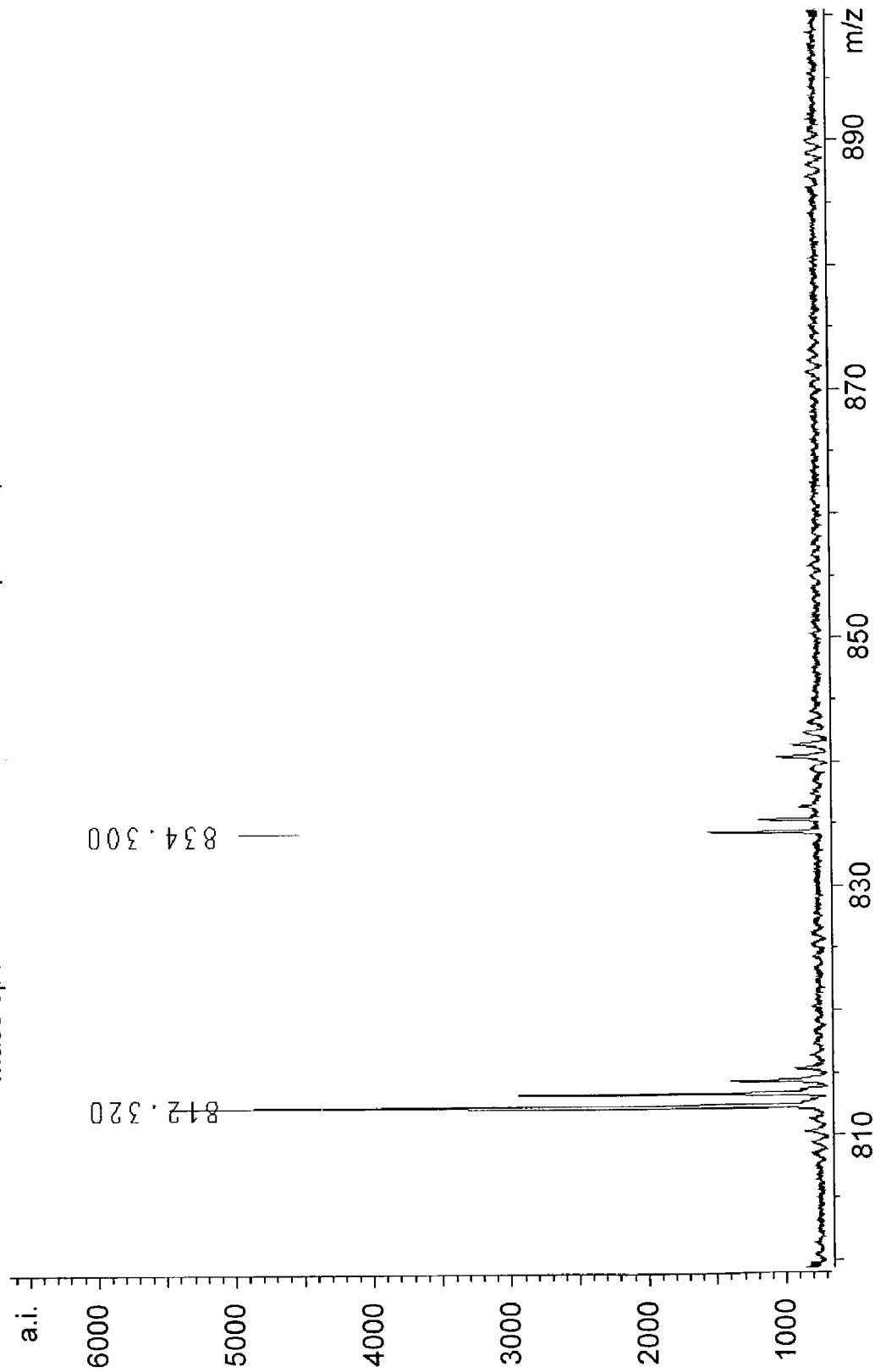

FIG. 10b Shows the MALDI MS analysis of the lactose-rhodamine conjugate as used in the experiment. The lactose-rhodamine molecular ion is detected as well as the sodium adduct molecular ion at 834 dalton.

Figure 10C:
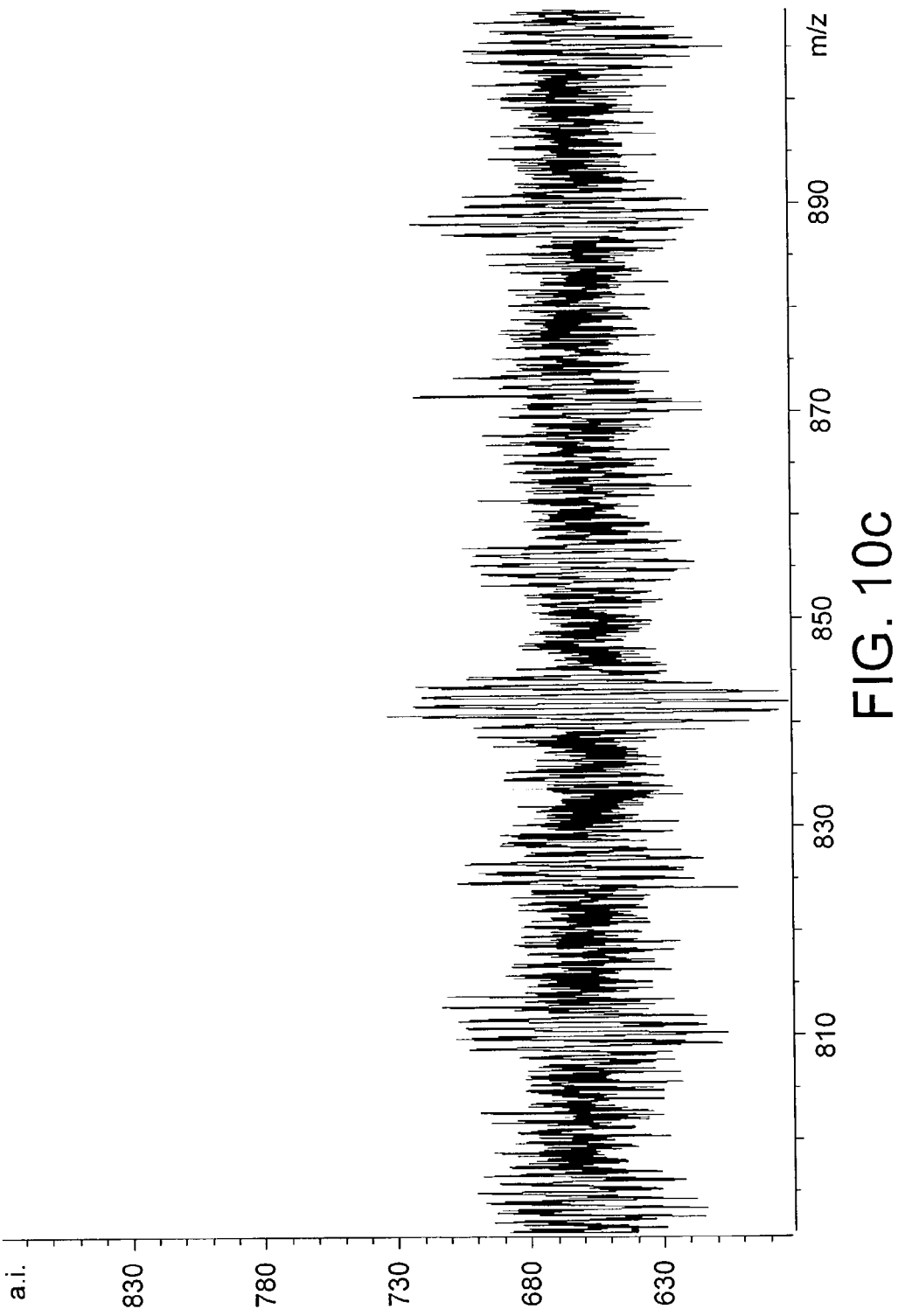

FIG. 10c A PEG-PLL neutravidin surface with the immobilised FK506 binding protein was overlaid with a 1 mM lactose-rhodamine conjugate and washed three times with 1 mM Tris-HCl pH pH 7.5 and overlaid with energy absorbing matrix molecules dissolved in acetone. The MALDI MS analysis shows no molecular ions of lactose rhodamine.

Table 1 shows the molecular weights of peptides which could be assigned to three protein by protein fingerprint analysis of a Glutathione-S-transferase digest. The molecular weights of the peptides were used to search NCBI nr database using the MASCOT search engine with a mass accuracy of 50 ppm. The matched proteins are glutathione-S-transferase, avidin and trypsin.

DETAILED DESCRIPTION

1. Preparation of a Probe According to One Aspect of the Invention.

1.1 Cleaning of Gold Coated Lass Slide and MALDI Probe.

A probe comprising a gold coated microscope glass slide or a MALDI probe was thoroughly cleaned before use with sequential washing steps in acetone, acetonitrile, double distilled water and dried under nitrogen.

1.2 Non Protein Binding Layer Incorporating Protein Binding Moieties Prepared and Deposited 1.2.1 PEG-PLL Derivative Synthesis PEG-PLL-Biotin:

100 mg poly-L-lysine average size 17–30 kda (Sigma, Dorset, UK) was reacted with 109 mg mPEG-SPA (Shearwater Corporation, Huntsville, Ala.) and 1.1 mg biotin PEG-CO-NHS in 100 mM carbonate buffer pH 9 for a period of 30 minutes. The reaction was terminated by dialysis in 1 mM Tris-HCl pH 7.5 over night. The product from this reaction was called 1% PEG-PLL-Biotin (1% PEG derivatives contain a biotin headgroup) and several other small ligand ratios were synthesized (1%, 2%, 10% and 20%).

PEG-PLL-Bleomycin:

10 mg of bleomycin B6 (Calbiochem,) was dissolved in 1 ml acetone and 7.5 mg EDC and NHS each was added. The pH of the reaction was adjusted with HCl at pH 3. In another reaction 99 mg poly-L-lysine was reacted with 11 mg DVS-PEG-CO-NHS and 100 mg mPEG-CO-NHS in 100 mM carbonate buffer pH 9. After 20 min both reactions were mixed and the pH was adjusted to pH 9 when necessary. The PEG-PLL-Bleomycin synthesis was cleaned up by a dialysis against a plentiful amount of 1 mM Tris-HCl pH 7.5 buffer over night. The product of this synthesis was called 10% PEG-PLL-Bleomycin indicating that approximately 10% of the PEG side chains are substituted with Bleomycin.

Freshly prepared affinity capture polymer, for example, 1% PEG-PLL-Biotin or 10% PEG-PLL-Bleomycin B6 was deposited onto the probe. The surface was then covered with Nesco film to evenly distribute the protein capture moiety over the probe. After 30 min the probe was washed in 1 mM Tris-HCL pH 7.5 and dried under nitrogen.

The PEG-PLL-Bleomycin B6 surface was ready for use.

1.3 Alternative Protein Capture Moeity Added if Required

The PLL-PEG-biotin has a neutravidin molecule bound to the biotin by adding 0.5 mg/ml neutravidin for one hour at RT in a humid chamber. The Probe was then rinsed with washing buffer, and washed twice with ample desalting buffer before it was dried under nitrogen. The surface was now ready to be used as a highly specific affinity capture of macromolecules carrying an appropriate affinity tag, e.g. Biotin or phleomycin/zeocin resitance binding protein.

2. Preparation of a Protein Microarray According to One Aspect of the Invention.

2.1 Tagged Proteins Produced

Purified mRNA from heart, liver or breast tissues are transcribed into cDNA using known techniques. The 3' end of the cDNA is made accessible to a 3' to 5' single-stranded exonuclease which digests one strand of the DNA. The reaction is controlled through manipulation of parameters such as time, temperature and salt concentration. The remaining single stranded region of DNA is then removed by a single-stranded nuclease such as mung bean nuclease, to leave a blunt end. The resulting truncated double stranded cDNA is then digested with a rare-cutting restriction enzyme which has a site at the 5' end of the cDNA, introduced during cDNA synthesis. The resulting cDNA fragment is then ligated to a DNA tag which encodes a marker of solubility. In this case, this is achieved by ligating the cDNA fragment into a vector which provides a tag 3' to the cDNA fragment. Transcription initiates upstream of the cloned cDNA and proceeds through the cDNA and downstream tag. When ligated in-frame and in the absence of stop codons, the resulting translation product consists of a polypeptide sequence derived from the cloned cDNA, fused to a tag which reports solubility of the fusion protein. This technique is applicable to both single cDNA and collections.

The version of the vector described here contains a tag which encodes the zeocin binding protein (ZBP), fused to Biotin Carboxyl Carrier Protein (BCCP) and the myc tag. The Applicant has demonstrated that both biotinylation of BCCP and the ability of the ZBP to confer resistance to Zeocin, is dependant on the solubility of the fusion protein. In addition, immediately upstream of the cloned cDNA, a small tag such as FLAG is encoded. The resulting expressed fusion protein contains tags at the N- and C-termini for quality control purposes. When the resulting modified cDNA library is transformed into E. coli and selected either on Zeocin or an analogue or is probed for biotinylation of BCCP, positive clones expressing soluble fusion proteins are identified.

2.2 Proteins Bound

In one experiment, human liver cDNA was subjected to this methodology and the resulting library expressed in *E. coli*. Approximately 5,000 clones expressing soluble fusion proteins were clonally isolated and individually subjected to fermentation. The cells were lysed and the resulting soluble, biotinylated proteins captured and purified on a streptavidin-coated surface in a single step. A protein microarray consisting of several thousand members was produced, reflecting the expressed complement of the liver at the time of harvest.

3. Analysis of a Protein Array According to One Aspect of the Invention.

3.1 Crystals of Energy Absorbing Molecules Prepared

Solutions of energy absorbing molecules for overlaying a protein microarray were prepared as set out below: i) to iii) and vii) are preparations according to one aspect of the invention whereas iv) to vi) are comparative preparations prepared according to prior art methods:

i) α-cyano-4-hydroxycinnamic acid (Sigma, Dorset, UK) was dissolved in acetone at saturating amounts and 300 nanoliter of the solution was used to overlay the analyte.

ii) Sinapinic acid (Sigma, Dorset, UK) was dissolved in acetone at saturating amounts and 300 nanoliter of the solution was used to overlay the analyte.

iii) Gentisic acid (Sigma, Dorset, UK) was dissolved in acetone at saturating amounts and 300 nanoliter of the solution was used to overlay the analyte.

iv) 10 mg/ml α-cyano-4-hydroxycinnamic acid (Sigma, Dorset, UK) was dissolved in 50% v/v acetonitrile, 0.1% trifluoroacetic acid as known in the art and 300 nanoliter of the solution is used to overlay the analyte on the probe.

v) Sinapinic acid (Sigma, Dorset, UK) was dissolved in ddH$_2$O at saturating amounts and 300 nanoliter of the solution is used to overlay the analyte.

vi) Gentisic acid (Sigma, Dorset, UK) was dissolved in ddH$_2$O at saturating amounts and 300 nanoliter of the solution was used to overlay the analyte.

vii) α-cyano-4-hydroxy-cinnamic acid (Sigma, Dorset, UK) is dissolved in 99% acetone v/v, 1% glycerol in saturating amounts. 3 nanoliter of the matrix formulation is then transferred onto the probe, which contains the analyte.

3.2 Generic Method for Microcrystalisation of Energy Absorbing Matrix Molecules The three examples of energy absorbing molecules prepared as described in 3.1 above were arrayed onto a protein microarray and the appearance at 100 fold magnification is illustrated in FIG. 1a. The acetone dissolved matrix i), ii) and iii) show a very homogenous crystal formation compared with the aqueous matrix iv), v) and vi) formulation currently used in the art.

Referring to FIG. 1a the left hand side slides show the acetone dissolved formulations whereas on the right hand side the aqueous matrix formulation are shown.

The new matrix formulation illustrated have proved significant in being able to generate protein microarrays (see FIG. 1b) because they allow a more efficient use of space on the probe surface, have enhanced flatness allowing greater mass accuracy, and furthermore increased amounts of matrix can be deposited on the probe to meet the needs of high analyte density.

FIG. 1b illustrates a probe according to one aspect of the invention with protein captured thereon (thus forming a protein microarray) with an energy absorbing matrix according to a further aspect of the invention overlaid. The α-cyano-4-hydroxy-cinnamic acid matrix was dissolved in acetone 99% v/v, 1% glycerol v/v and arrayed onto a gold coated microscope slide. After solvent evaporation, matrix crystals are formed. In contrast to the crystals formed by the deposit of aqueous solutions the nonaqueous solvent formulation of matrix lead to a very homogeneous and flat crystal layer. Because of this the analyst looking at the spots can "hit" the analyte within the "spot" and consequently the spot can be made smaller enabling the miniaturization and production of a microarray because of the resulting high spatial density, which could not be created using aqueous matrix formulations. This is a significant development in the creation of mass spectrometric compatible protein microarrays.

4. Protein Array Subjected to MALDI and Different Methods of Use.

4.1 Surface Capture of Substantially Pure Tagged Biological Macromolecules

EXAMPLE 1

Affinity capture of a variety of tagged proteins can be demonstrated using for example PEG-PLL-biotin or PEG-PLL-Bleomycin B6 as the protein capturing moieties.

FIGS. 2, a and b show the mass spectra acquired from a protein microarray demonstrating respectively the capture of 1500 and 15 femtogram of biotin tagged insulin. The biotin tagged insulin was arrayed onto an affinity capture surface on a gold coated microscope glass slide in a 3 nanoliter volume using 300 micrometer pins (Q-Array, Genetix, New Milton, UK). The gold coated PEG-PLL-Biotin Neutravidin surface, was washed three times with 1 mM Tris-HCl pH 7.5, dried under a stream of nitrogen and overlaid with 3 nanolitre of α-cyano-4-hydroxy-cinnamic acid dissolved in 99% acetone v/v, 1% glycerol resulting in a spot with an radius of approximately 200 micrometer. The probe was analysed with a mass spectrometer MALDI TOF mass spectrometer. Several biotin tagged insulin peaks are visible due to the different degree of biotinylation. Two additional peaks are observed at 7300 dalton and 14600 dalton and these are Neutravidin [MH]$^+$and [MH]$^{2+}$.

This example demonstrates the protein microarray capability of this system and shows the versatility of immobilising analytes on the probe surface for removal of salt that otherwise could interfere with the formation of gaseous ions as known in the art. Together with the new matrix formulation it demonstrates the capability of manufacturing protein microarrays for mass spectrometric analysis.

4.2 Surface Capture and Detection of Recombinant Protein on a Probe Surface From a Crude Extract

EXAMPLE 2

A PLL-PEG-biotin neutravidin surface on a MALDI target is overlaid with 500 nanoliters of a biotinylated protein mixture derived from an E. coli lysate expressing a human recombinant protein in conjunction with a sequence tag in this case Biotin carboxyl carrier protein (BCCP) from E. coli. The protein was captured for a period of 2 hours on the surface, washed twice with washing buffer followed by two washes with desalting buffer, and overlaid with 300 nanoliters of an energy absorbing matrix, namely saturated α-cyano-4-hydroxycinnamic acid in acetone. The mass spectrum acquired in linear mode using the delayed extraction technique at low laser power is illustrated in FIG. 5. The advantage of this method is that the sample can be applied as a complex mixture of proteins and after washing only the molecules of interest remain. Secondly the analyte is captured in a spatially defined position before it is released from the affinity capture surface by the addition of matrix.

4.3 Capture, Detection and Identification of Recombinant Protein on Probe Using a Depredation Process

EXAMPLE 3

FIG. 6 shows the peptide fingerprint analysis of Glutathione-S-transferase-Biotin Carboxyl Carrier Protein (GST-BCCP). A bacterial crude lysate containing the fusion protein and bacterial proteins was placed on the MALDI target previously coated with PEG-PLL-biotin and neutravidin. The BCCP fusion partner of GST contained a biotinylation consensus sequence such that it becomes biotinylated when expressed in E. coli. allowing the fusion protein to bind specifically to the PEG-PLL-biotin neutravidin surface, whilst allowing the bacterial proteins to be washed away with buffer. For identification purpose the surface captured protein was digested by overlaying it with trypsin and analysed by MALDI MS. A protein fingerprint analysis revealed 12 peptides belonged to GST from Schistosoma mansoni, 4 peptides belonging to Neutravidin and 3 to trypsin (see table 1), but no bacterial protein was identified using the remaining un-matched peptides. This experiment demonstrates that PEG-PLL-biotin and neutravidin can be used to purify a protein from a crude mixture of protein in a single step on a MALDI target. Taken together this experiment paves the way for protein microarray production where the protein content on the array is derived from a bacterial expression system without the need for an initial pre-purification step.

EXAMPLE 4

FIG. 9a shows a mass spectrum of the biotinylated lectin from Triticum vulgaris (WGA) captured onto a PEG-PLL-Biotin Neutravidin surface. The lectin was then probed with the glycoprotein Fetuin and the MALDI target was washed and desalted. The mass spectrum reveals molecular ions of neutravidin at 14300 and 28600 dalton, the lectin was detected at 17700 and 35500 and Fetuin derived peaks were observed at 44163. Furthermore, there are two peaks present at 25943 and 32158 that had not been observed when the lectin was analysed in the absence of Fetuin and they might represent degradation products of the lectin since we observed several bands upon gel electrophoretic analysis of the Fetuin preparation. However the higher molecular weight band represented the main fraction of the protein. In FIG. 9b the MALDI TOF spectrum of biotinylated Arachis hypogea lectin captured on a PEG-PLL-Biotin Neutravidin surface is shown. The lectin was probed with the same Fetuin solution as in FIG. 9a. However the lectin from Arachis hypogea has a different binding affinity towards carbohydrates then the *Triticum vulgaris* lectin and it therefore enriched specifically the small fraction of glycoprotein that had no terminal sialic acid. The mass spectrum contains peaks derived from neutravidin at 14300 and peaks from the lectin at 25774 and 51461 dalton and two peaks derived from Asialofetuin are present at 40136 and 42731 consistent with the loss of 4 and 13 sialic acid groups. The last two experiments demonstrate the detection and analysis of protein-glycoprotein interactions on a protein array by mass spectrometry.

4.4 Detection of Small Molecules on Protein Microarrays

EXAMPLE 5

To demonstrate the capability of small molecule detection in the presence of the PEG-PLL-biotin and Neutravidin three small molecules used in pharmacology and toxicology were spiked onto the array. The molecules Cyclosporin, Ketoconazole and Quinidine were identified at their corresponding molecular weight.

A PEG-PLL-biotin coated probe was incubated with a solution of Neutravidin and washed extensively with washing buffer (1 mM Tris-HCl pH 7.5 with 0.1% Triton X-100) and desalting buffer (1 mM Tris-HCl pH 7.5.), dried and overlaid with energy absorbing matrix and then analysed with MALDI TOF mass spectrometry.

The mass spectra (FIGS. 3a, 3b and 3c) show the specific capture of Neutravidin $[MH]^+$ and $[MH]^{2+}$ at 7310 and 14652 dalton.

EXAMPLE 6

In a further example the binding of a small molecule to a protein is demonstrated in FIGS. 10a, b, and c. The lactose rhodamine conjugate was specifically retained on a PEG-PLL-Neutravidin *Arachis hypogea* lectin surface whereas it could not be detected on a PEG-PLL-Neutravidin FK506 binding protein surface. This is another example for the detection of a small molecule protein interaction. The example is surprising since binding constant for lactose and this lectin is in the millimolar range, suggesting that the presence of the rhodamine moeity has increased the affinity of the small molecule ligand.

4.5 Detection of a Reactant on a Protein Microarray

EXAMPLE 7

ATP was enzymatically synthesized from the reaction of ADP, creatine phosphate and creatine phosphate kinase in 25 mM ammonium bicarbonate at pH 7.4. $[ADP]^-$ was detected at 427.6 dalton and $[ADP+Na]^-$ 449.6 dalton (see FIG. 4a). The products of the creatine phosphate kinase reaction were detected at 507.6, 529.6, 551.6 and 573.8, which fits well with the expected molecular weight of $[ATP]^-$ and three ATP sodium adducts $[ATP\ Na]^-$, $[ATP\ Na_2]^-$ and $[ATP\ Na_3]^-$.

Control reactions in which either one of the substrates ADP or creatine phosphate or the enzyme creatine phosphate kinase were omitted didn't show ATP peaks.

4.6 Detection of a Reactant on a Protein Microarray

EXAMPLE 8

The oxidation of drug-like small molecules by human cytochrome P450 enzymes is the usual first step in the metabolism of such compounds.

Here, the oxidation of dibenzylfluorescein by cytochrome P450 3A4 was studied with MALDI MS and the results illustrated in FIG. 4b. Dibenzylfluorescein (DBF) was detected at 513.795 [MH]+ and a metastabile oxidation product was observed at 530.069, which indicates the addition of one oxygen. The resulting molecule is known to be chemically unstable and therefore monobenzylfluorescein (MBF) and their oxidation products can be observed at 444.912 [MH]+, 460.890 [MH+O]+ and 476.855 [MH+2O] dalton.

This experiments shows the suitability of a protein arrays to detect biological catalysis and to assign function to biological polypeptides captured on protein arrays.

The mass spectra from the figures listed below had been obtained on
1. Bruker Daltonic gold targets #26993 (FIGS. 3a, 3b, 3c, 4, 5)
2. Bruker Daltonic glass target #26754 (FIG. 6)
3. Bruker Daltonic MTP 384 target milled out to harbor a gold coated microscope 30×75 mm glass slide (FIGS. 2a, 2b)

What is claimed is:

1. A probe, for use with a laser desorption/ionisation mass spectrometer, comprising a support having an electroconductive target surface thereon wherein the target surface comprises a layer that is resistant to non-specific protein binding, said layer incorporating protein repellant molecules and one or more high affinity analyte capture moieties, wherein said high affinity analyte capture moieties are incorporated homogeneously in said layer in small proportions relative to the protein repellant molecules.

2. A probe as claimed in claim 1 wherein the support is a glass slide, or a MALDI target.

3. A probe as claimed in claim 1 wherein the electroconductive surface comprises a metal or a semi conductor.

4. A probe as claimed in claim 3 wherein the metal is selected from gold, silver, platinum, iridium, iron, nickel, cobalt, copper or a mixture or alloy thereof and the semi conductor is selected from silicon, graphite or germanium.

5. A probe as claimed in claim 1 wherein the high affinity analyte capture moieties are protein capture moieties.

6. A probe as claimed in claim 5 wherein the high affinity protein capture moieties are not an antibody.

7. A probe as claimed in claim 5 wherein at least one high affinity protein capturing moiety binds biotin or a bleomycin resistance protein.

8. A probe as claimed in claim 7 wherein the high affinity protein capturing moiety is streptavidin, avidin, neutravidin or bleomycin.

9. A method of producing a protein microarray for use with laser desorption ionization mass spectrometer comprising providing a probe as claimed in claim 5 and depositing protein in registration with the protein capturing moieties in the discrete target area.

10. A method of analysing a protein microarray as claimed in claim 9 comprising subjecting the protein microarray to laser desorption/ionisation mass spectrometry.

11. A method as claimed in claim 10 wherein the laser desorption/ionisation mass spectrometry is matrix assisted laser desorption/ionisation mass spectrometry MALDI.

12. A method as claimed in claim 11 wherein energy absorbing molecules are deposited over the whole surface or in registration with the discrete target area on which a protein has been captured.

13. A method as claimed in claim 12 wherein energy absorbing molecules are deposited in registration with the discrete target area on which a protein has been captured.

14. A method as claimed in claims 12 or 13 in which the energy absorbing molecules are deposited in a maimer which denatures and thus unbinds the protein from the protein capturing moieties leaving the denatured protein in close proximity to the protein capture moiety on the surface.

15. A method as claimed in any of claims 12 or 13 wherein the energy absorbing molecules are present as a homogenous layer in the discrete target area in registration with the protein capturing moieties and captured protein.

16. A method as claimed in claim 15 wherein the homogenous layer is substantially continuous such that individual crystals are not visible at a 100 fold magnification and there are no visible gaps between neighboring crystals.

17. A method as claimed in claim 15 wherein the homogenous layer is of a substantially uniform depth such that there is no apparent variation in crystal size at 100 fold magnification.

18. A method as claimed in claim 12 wherein the energy absorbing molecules are deposited onto the surface in a non aqueous solvent and the non aqueous solvent is evaporated off.

19. A method as claimed in claim 18 wherein the non aqueous solvent is an organic solvent.

20. A method as claimed in claim 19 wherein the organic solvent is acetone or butanone.

21. A method as claimed in claim 12 wherein the non aqueous solvent includes a modifier which controls the rate of evaporation such that evaporation of the non aqueous solvent occurs after the energy absorbing molecules are deposited.

22. A method as claimed in claim 21 wherein the modifier which controls the rate of evaporation is glycerol, polyetheleglycol or thioglycerol.

23. A method as claimed in claim 12 wherein the energy absorbing molecules are deposited in a mixture of from 80–99.9%, preferably 99%, non aqueous solvent, preferably acetone, to 20–0.1%, preferably 1%, modifier, preferably glycerol (vol/vol).

24. A method as claimed in claim 12 wherein the energy absorbing molecules comprises crystals of α-cyano-4-hydroxy-cinnamic acid, sinapinic acid, gentisic acid, nifidine, succinic acid, 1,8,9,-anthracenitriol, 3-Indoleacrylic acid, 2-(hydroxyphenylazo) benzoe-acid, 4-nitroanilin and combinations thereof.

25. A method of analysis by laser desorption/ionisation mass spectrometry comprising the steps of:
   a) providing a probe as claimed in claim 5;
   b) bringing said probe into contact with one or more proteins;
   c) performing laser desorption/ionisation mass spectrometry on the proteins on the surface of the probe.

26. The method of claim 25 which comprises between step b) and c) an additional step of removing unbound molecules from the probe by washing.

27. The method of claim 26 wherein said one or more proteins are contained in a mixture of proteins.

28. The method of claim 25 which is a method for identifying a protein on the surface of the probe and which comprises the additional steps of:
   d) determining the mass of the protein molecule;
   e) performing a digestion upon a replicate sample of said protein on a further probe or probe surface; and
   f) performing laser desorption/ionisation mass spectrometry on the peptides resulting from step e) to identify said proteins.

29. The method of claim 25 which is a method of analysing the function of a protein on the surface of the probe and a molecule interacting with said protein and which comprises the additional steps instead of step c) of:
   c) bringing a protein on the probe surface into contact with one or more test molecules;
   d) removing unbound test molecules from the probe surface;
   e) performing laser desorption/ionisation mass spectrometry on the protein and any bound molecule to determine the identity of the protein and/or test molecule.

30. The method of claim 29 wherein the test molecule is a small molecule, protein or nucleic acid.

31. The method of claim 25 which is a method of analysing the function of a protein and which comprises the additional steps of:
   c) bringing a protein on the probe surface into contact with one or more test substrates;
   d) performing laser desorption/ionisation mass spectrometry on the protein and test substrates to determine the presence and/or identity of products of catalysis of said test substrates by the protein.

32. A probe as claimed in claim 1 wherein the high affinity analyte capture moieties are small molecules.

33. A probe as claimed in claim 32 wherein the small molecules are less than 2 kDa, preferably less than 1 kDa, more preferably less than 500 Da.

34. A probe as claimed in claim 1 wherein the binding affinity (Kd) between the analyte capture moiety and its binding partner is at least $10^{-7}$M, more preferably at least $10^{-9}$M, more preferably at least $10^{-12}$M and more preferably still at least $10^{-5}$M.

35. A probe as claimed in claim 1 wherein the high affinity analyte capture moiety is attached directly to the electroconductive target surface.

36. A probe as claimed in claim 1 wherein the high affinity analyte capture moiety is indirectly attached to the electroconductive target surface.

37. A probe as claimed in claim 36 wherein the high affinity analyte capture moiety is attached via one or more linker molecules.

38. A probe as claimed in claim 37 wherein the linker molecules comprises a poly amino acid or an alkane thiol.

39. A probe as claimed in claim 38 wherein poly amino acid is poly-L-lysine, poly-L-aspartic acid, poly-L-glutamic acid or mixtures of any other known amino acids with the three aforementioned amino acids.

40. A probe, as claimed in claim 36, wherein the high affinity analyte capture moiety comprises a capturing element and a linker.

41. A probe as claimed in claim 40 wherein at least one protein capturing element binds biotin or a bleomycin resistance protein.

42. A probe, as claimed in claim 40, wherein said capturing element is selected from the group consisting of biotin, bleomycin, neutravidin, biotin carboxyl carrier protein, and zeocin binding protein, streptavidin and avidin.

43. A probe as claimed in claim 42 wherein poly amino acid is poly-L-lysine, poly-L-aspartic acid, poly-L-glutamic acid or mixtures of any other known amino acids with the three aforementioned amino acids.

44. A probe, as claimed in claim 40, wherein the linker molecule comprises poly amino acid or an alkane thiol.

45. A probe as claimed in claim 40 wherein the high affinity analyte capture moiety is selected from the group consisting of a poly-L-lysine polyethylenglycol biotin polymer, poly-L-lysine polyethylenglycol bleomycin polymer, poly-L-lysine polyethylenglycol biotin neutravidin polymer.

46. A probe as claimed in claim 1 wherein the layer which is otherwise substantially resistant to non specific protein binding comprises a polymer or a self assembled monolayer (SAM) which is responsible for the generally protein repellant nature of the layer.

47. A probe as claimed in claim 46 wherein the polymer comprises polyethylene glycol (PEG), dextran, polyurethane or polyacrylamide.

48. A probe as claimed in claim 47 wherein the polymer is bound to the probe surface via one or more linker molecules.

49. A probe as claimed in claim 48 wherein the high affinity analyte capturing moiety is attached to the surface via the polymer and/or the linker molecules.

50. A probe as claimed in claim 1 wherein a single common high affinity analyte capture moiety is provided on the surface.

51. A probe as claimed in claim 1 wherein a plurality of different high affinity analyte capturing moieties are provided on the surface.

52. A probe as claimed in claim 1 further comprising a captured analyte.

53. A probe as claimed in claim 1 wherein the high affinity analyte capturing moieties are homogeneously disposed across substantially the whole of the surface.

54. A probe as claimed in claim 1 which can bind an analyte at a concentration of below $10^{15}$ molecules per 1000 $\mu m^2$, more preferably at a concentration of below $10^{12}$ molecules per 1000 $\mu m^2$, more preferably at a concentration of below $10^9$ molecules per 1000 $\mu m^2$, more preferably still at a concentration of below $10^6$ molecules per 1000 $\mu m^2$.

55. A probe as claimed in claim 1, wherein the proportion of said high affinity analyte capture moieties relative to said protein repellant molecules in said layer is less than 20%.

56. A probe as claimed in claim 1 or claim 55, wherein the proportion of said high affinity analyte capture moieties relative to said protein repellant molecules in said layer is in the range 1–20%.

57. A probe in claim 56, wherein the proportion of said high affinity analyte capture moieties relative to said protein repellant molecules in said layer is 1%, 2%, 10% or 20%.

58. A probe as claimed in claim 1, wherein said target surface comprises a microarray having a plurality of discrete target areas, and said high affinity analyte capturing moieties are homogeneously disposed in discrete target areas.

59. A probe as claimed in claim 58 wherein the high affinity analyte capture moieties are disposed in the discrete target areas in a defined orientation.

60. A probe as claimed in claim 58 wherein the analyte capturing moieties are homogenously disposed in only the discrete target areas.

61. A probe as claimed in claim 58 wherein the surface in the discrete target areas is substantially planar.

62. A probe as claimed in claim 61 wherein the discrete target areas are flat bottomed wells.

63. A probe as claimed in claim 1, further comprising a captured analyte, which analyte is captured in a plurality of discrete target areas as a microarray.

64. A probe as claimed in claim 58 or 63 wherein the plurality of discrete target areas are arranged in a spatially defined manner.

65. A probe as claimed in claim 58 or 63 wherein each discrete target area has an area of less than 1000 $\mu m^2$, more preferably still less than 500 $\mu m^2$, and more preferably still less than 100 $\mu m^2$.

66. A probe as claimed in claim 58 or 63 wherein each discrete target area has an area of less than 785 $\mu m^2$ more preferably less than 392 $\mu m^2$ more preferably still less than 78 $\mu m^2$.

67. A probe as claimed in claim 58 or 63 wherein the discrete target areas are substantially circular.

68. A probe as claimed in claim 58 or 63 wherein the discrete target areas are arranged in matrices.

69. A probe as claimed in claim 68 wherein there are a plurality of matrices on the target surface.

70. A probe as claimed in claim 68 wherein the matrices comprise at least 2 rows and 2 columns of discrete target areas.

71. A probe as claimed in claim 58 or 63 comprising at least 10, more preferably at least 100, more preferably still at least 1000, and more preferably still at least 10000 discrete target areas.

72. A probe as claimed in claim 58 or 63 wherein there is a spacing between adjacent discrete target areas in a matrix of less than 1 mm.

73. A probe as claimed in claim 63 wherein the captured analyte comprises a protein.

74. A probe as claimed in claim 73 wherein the protein is a fusion protein.

75. A probe as claimed in claim 74 wherein the fusion protein comprises a biotin carboxyl carrier protein (BCCP).

76. A probe as claimed in claim 74 wherein the fusion protein comprises a phleomycin/zeocin resistance protein.

77. A probe as claimed in claim 63 wherein the captured analyte has a further molecule bound to it.

78. A probe as claimed in claim 77 wherein the further molecule is either a small molecule, a protein or a nucleic acid.

79. A probe as claimed in claim 63 wherein the analyte is printed onto the surface.

80. A probe as claimed in claim 79 wherein the analyte is printed using, inkjet printing, piezo electric printing or contact printing.

81. A probe as claimed in claim 80 wherein for the contact printing the analyte is applied using a split pin, solid pin or a hollow pin.

* * * * *